United States Patent
Divine et al.

(10) Patent No.: US 9,968,310 B2
(45) Date of Patent: May 15, 2018

(54) MULTI-DETECTOR IMAGING SYSTEM WITH X-RAY DETECTION

(71) Applicant: General Electric Company, Schenectady, NY (US)

(72) Inventors: Lucas Jason Divine, Wauwatosa, WI (US); Jean-Paul Bouhnik, Tirat Carmel (IL); Joseph Lacey, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 576 days.

(21) Appl. No.: 14/616,217

(22) Filed: Feb. 6, 2015

(65) Prior Publication Data

US 2016/0081635 A1    Mar. 24, 2016

Related U.S. Application Data

(63) Continuation-in-part of application No. 14/494,973, filed on Sep. 24, 2014.

(51) Int. Cl.
*A61B 6/00* (2006.01)
*A61B 6/06* (2006.01)
*A61B 6/03* (2006.01)

(52) U.S. Cl.
CPC .............. *A61B 6/06* (2013.01); *A61B 6/032* (2013.01); *A61B 6/037* (2013.01); *A61B 6/4266* (2013.01);
(Continued)

(58) Field of Classification Search
CPC ........... A61B 6/032; A61B 6/037; A61B 6/06; A61B 6/4266; A61B 6/4417; A61B 6/488;
(Continued)

(56) References Cited

U.S. PATENT DOCUMENTS

| 4,920,552 A | 4/1990 | Hermens |
| 5,338,936 A | 8/1994 | Gullberg et al. |

(Continued)

OTHER PUBLICATIONS

International Search Report and Written Opinion for corresponding PCT Application No. PCT/US2016/016382, dated May 10, 2016; 15 pages.

*Primary Examiner* — Irakli Kiknadze

(74) *Attorney, Agent, or Firm* — Dean D. Small; The Small Patent Law Group, LLC

(57) ABSTRACT

An imaging system is provided that includes a gantry, a plurality of image detectors, an x-ray source, an adjustable source collimator, and at least one processor. The image detectors are radially spaced around a circumference of the bore such that gaps exist between adjacent image detectors. The x-ray source transmits x-rays across the bore towards at least two of the image detectors. The adjustable source collimator is interposed between the x-ray source and a center of the bore, and is configured to block a portion of the x-rays produced by the x-ray source The at least one processor is configured to control the adjustable source collimator to dynamically adjust a range of x-rays that are blocked by the adjustable source collimator along the fan angle during transmission of x-rays from the x-ray source and acquisition of computed tomography (CT) information.

27 Claims, 25 Drawing Sheets

(52) U.S. Cl.
CPC ............ *A61B 6/4417* (2013.01); *A61B 6/488* (2013.01); *A61B 6/5235* (2013.01)

(58) Field of Classification Search
CPC ......... A61B 6/5235; A61B 6/469; A61B 6/54; A61B 6/541; A61B 6/0407; A61B 2090/374; A61B 2090/3762; A61B 6/12; A61B 6/4007; A61B 6/4291; A61B 6/4435; A61B 6/4014; A61B 6/4078; A61B 6/4241; A61B 6/027; A61B 6/542; A61B 6/405; A61B 6/4035; A61B 6/4085; A61B 6/0457; A61B 6/4028; A61B 6/4042; A61B 6/4275; A61B 6/4441; A61B 6/4488; A61B 6/482; A61B 6/484
USPC ...................... 378/4, 5, 15, 19, 62
See application file for complete search history.

(56) References Cited

U.S. PATENT DOCUMENTS

| | | | |
|---|---|---|---|
| 5,376,795 A | 12/1994 | Hasegawa et al. | |
| 6,399,951 B1 | 6/2002 | Paulus et al. | |
| 7,323,689 B2 | 1/2008 | Hawman | |
| 7,374,337 B2 | 5/2008 | Yunker | |
| 8,139,713 B2 | 3/2012 | Janbakhsh | |
| 8,184,775 B1 | 5/2012 | Fan et al. | |
| 8,213,568 B2 | 7/2012 | Heuscher et al. | |
| 8,503,603 B2 | 8/2013 | Tancredi et al. | |
| 2002/0090050 A1 | 7/2002 | Nutt et al. | |
| 2007/0019784 A1 | 1/2007 | Ting | |
| 2010/0091940 A1* | 4/2010 | Ludwig | A61B 6/025 378/22 |
| 2011/0058645 A1 | 3/2011 | Heuscher | |
| 2012/0043481 A1* | 2/2012 | Mansfield | G21K 1/046 250/492.1 |
| 2012/0085912 A1 | 4/2012 | McCroskey et al. | |
| 2012/0128120 A1* | 5/2012 | De Man | A61B 6/032 378/16 |
| 2013/0003936 A1 | 1/2013 | Grodzina et al. | |
| 2013/0343513 A1* | 12/2013 | Noo | A61B 6/027 378/16 |
| 2014/0177782 A1* | 6/2014 | Herold | A61B 6/032 378/4 |
| 2014/0270056 A1* | 9/2014 | Zou | A61B 6/032 378/19 |

* cited by examiner

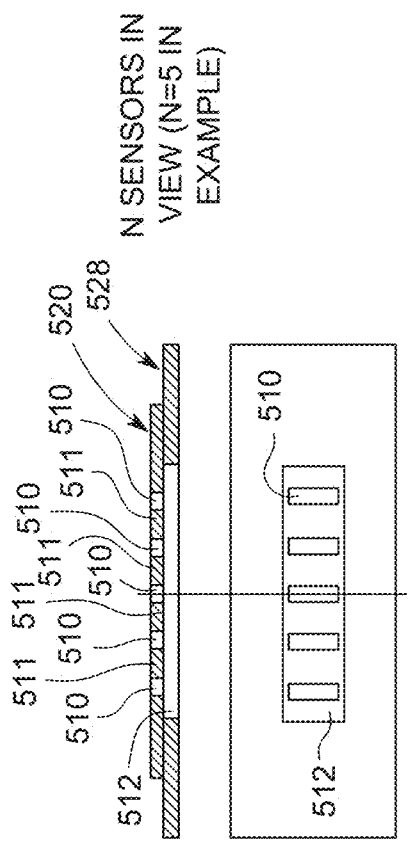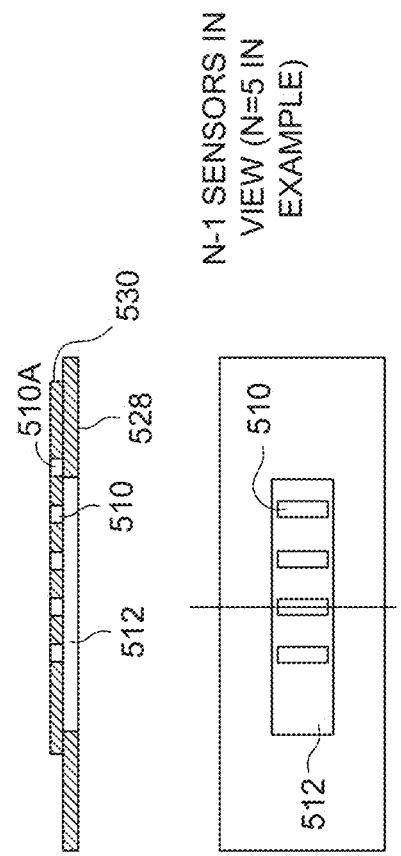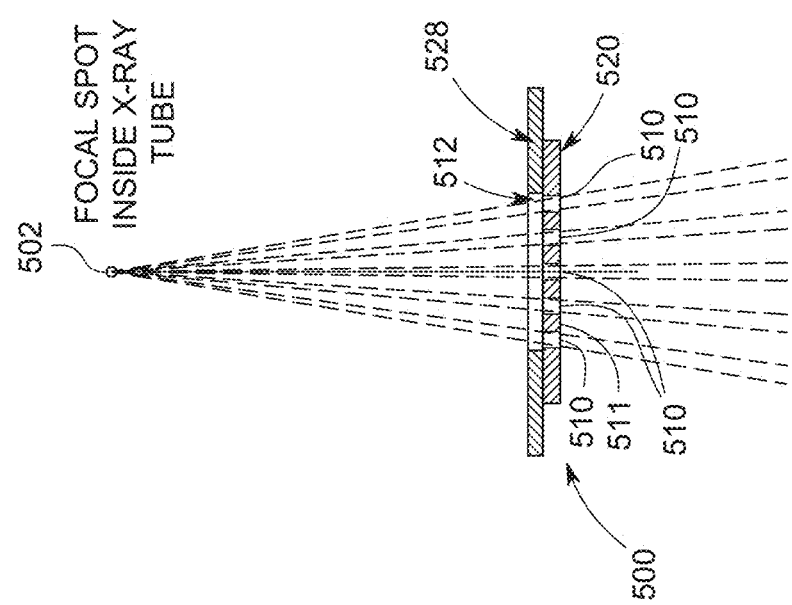

MULTI-DETECTOR IMAGING SYSTEM WITH X-RAY DETECTION

CROSS-REFERENCE TO RELATED APPLICATIONS

This application is a continuation in part of U.S. application Ser. No. 14/494,973, filed Sep. 24, 2014, entitled "Multi-Detector Imaging System With X-Ray Detection," the subject matter of which is incorporated herein in its entirety.

BACKGROUND

The subject matter disclosed herein relates generally to medical imaging systems, and more particularly to diagnostic imaging systems which combines Computed Tomography (CT) with a Nuclear Medicine (NM) Single Photon Emission Computed Tomography (SPECT) system.

In CT imaging, a patient is placed in a gantry. The gantry can comprise a stationary frame for supporting a rotary member. The rotary member includes a central opening, or bore, large enough to receive a patient extending along the scanning axis. The rotary member is rotated about a patient during a scanning or imaging procedure. An x-ray tube can be positioned on the rotary member diametrically across the central opening from an array of x-ray detectors. As the rotary member rotates, the x-ray tube projects a beam of energy, or x-rays, along a scan plane, through a patient, and to the detector array. By rotating the x-ray source about the scanning axis and relative to the patient, x-rays are projected through a patient from many different directions. An image of the scanned portion of a patient can be constructed from data provided by the detector array using a computer.

In NM imaging, such as SPECT or PET imaging, radiopharmaceuticals are administered internally to a patient. Detectors (e.g., gamma cameras), typically installed on a gantry, capture the radiation emitted by the radiopharmaceuticals and this information is used, by a computer, to form images. The NM images primarily show physiological function of, for example, the patient or a portion of the patient being imaged.

In a NM system, it can be advantageous to collect CT information for purposes of attenuation correction, body shape planning, scouting specific organs, and other known benefits of CT data. It is needed to provide such a system that is low-cost and efficient.

BRIEF DESCRIPTION

In accordance with an embodiment, an imaging system is provided that includes a gantry having a bore extending therethrough; a plurality of image detectors attached to the gantry and radially spaced around a circumference of the bore such that gaps exist between image detectors along the circumference of the bore; an x-ray source attached to the gantry, wherein the x-ray source transmits x-rays across the bore towards at least two of the image detectors; wherein one or more detectors detect both emission radiation and x-ray radiation.

The system can further include a stationary structure and a rotary member; wherein the x-ray source is attached to the rotary member and the plurality of image detectors are attached to the stationary structure; and wherein the rotary member rotates to allow the x-ray source to orbit an imaging subject inside the bore, each image detector further comprising a sweep motor; a detector head comprising detector elements; and wherein, if the image detector is in an x-ray transmission fan beam, the sweep motor adjusts the angle of the detector head to be directed at the x-ray source. The image detectors can further comprise a radial motor for extending the image detector closer to and retracting the image further from a region of interest; and wherein, if the image detector is not in the x-ray transmission fan beam, the sweep motor adjusts an angle of the detector head to be directed at the region of interest and the radial motion motor extends or retracts the image detector based on its distance to the region of interest.

In an alternative embodiment, the plurality of image detectors are attached to the rotary member and the x-ray source is attached to the stationary structure; and wherein the rotary member rotates to allow the imaging detectors to orbit an imaging subject inside the bore. Alternatively, the gantry can include two rotary members wherein both rotary members are annular; and wherein the plurality of image detectors are attached to the first rotary member and the x-ray source is attached to the second rotary member. In this case the plurality of detectors could rotate around the bore on an outer circumference; and the x-ray source could rotate around the bore on an inner circumference.

The gaps in the system may receive radiation such that the transmitted x-rays are transmitted in a fan beam; and more than fifty percent of the fan beam angle is gap transmission in that x-rays enter the gaps and do not hit an image detector. In this case the system could further comprise a source collimator; and wherein a processor in the system directs the collimator to block gap transmissions. The image detectors can be regularly spaced around the circumference of the bore such that the gaps between image detectors are substantially equivalent. Alternatively the image detectors can be irregularly spaced around the circumference of the bore such that the gaps between image detectors are not equivalent.

The system contains an image reconstruction module that: receives emission radiation and x-ray radiation from the plurality of image detectors and generates medical images; and outputs the medical images to a display or a memory device. The image reconstruction module can use the emission radiation to reconstruct a first medical image and uses the x-ray radiation to perform attenuation correction on the first medical image to generate a second medical image. If image detectors further comprise a sweep motor; a detector head comprising detector elements; and a radial motor for extending and retracting the image detector; then the image reconstruction module can use the x-ray radiation to determine the location of a region of interest; the radial motor extends the image detector towards the region of interest; the sweep motor adjusts the detector head angle to be directed towards the region of interest; and the detector elements detect emission radiation. Further, the image reconstruction module can use the emission radiation to reconstruct a second medical image and uses the x-ray radiation to determine an anatomical shape related to the second medical image.

Additional features of the system can include the configurations that the x-ray source transmits low-power x-rays, the image detectors further comprise detector elements made from Cadmium Zinc Telluride (CZT), the system has a second x-ray source attached to the gantry, the x-ray source and the plurality of image detectors share an X-Y plane, the image detectors are photon counting detectors, or the emission radiation is single photon emission computed tomography (SPECT) radiation.

In an embodiment, the system can activate the image detectors that are in an x-ray transmission fan beam and does not activate the image detectors that are outside of the x-ray transmission fan beam.

In an embodiment, a gantry is provided including a bore extending therethrough; a rotary member; an x-ray source attached to the rotary member, wherein the rotary member rotates the x-ray source around the circumference of the bore; a plurality of image detectors attached to the gantry and radially spaced around a circumference of the bore such that gaps exist between image detectors along the circumference of the bore; each image detector further comprising a detector head and a sweep motor to adjust the angle of the detector head; wherein at least two sweep motors adjust the angle of the respective detector head towards the x-ray source; and wherein the image detectors detect x-ray radiation.

In an embodiment, an imaging method is provided including rotating an x-ray source around the circumference of a gantry bore; receiving transmitted x-ray radiation at a plurality of image detectors spaced evenly around the circumference of the bore such that gaps exist between image detectors along the circumference of the bore; receiving emission radiation at a plurality the plurality of image detectors; generating a medical image based on the emission radiation and x-ray radiation. The method can include that the emission data is used to generate an intermediate image; and the x-ray data is used to perform attenuation correction on the intermediate image to generate the medical image. The method can also include determining a region of interested based on the x-ray radiation; and adjusting the angle of at least two detector heads to be directed towards the region of interest.

In accordance with an embodiment, an imaging system is provided that includes a gantry, a plurality of image detectors, an x-ray source, an adjustable source collimator, and at least one processor. The gantry has a bore extending therethrough. The plurality of image detectors are attached to the gantry and radially spaced around a circumference of the bore such that gaps exist between adjacent image detectors along the circumference of the bore. At least one image detector detects both emission radiation and x-ray radiation. The x-ray source is attached to the gantry, and transmits x-rays across the bore towards at least two of the image detectors. The adjustable source collimator is interposed between the x-ray source and a center of the bore, and is configured to block a portion of the x-rays produced by the x-ray source along a fan angle in a scanning direction defined by the circumference of the bore. The at least one processor is operably coupled to the adjustable source collimator. The at least one processor is configured to control the adjustable source collimator to dynamically adjust a range of x-rays that are blocked by the adjustable source collimator along the fan angle during transmission of x-rays from the x-ray source and acquisition of computed tomography (CT) information by the at least two of the image detectors.

In accordance with an embodiment, a method of acquiring computed tomography (CT) information is provided for an imaging system having a gantry having a bore extending therethrough, a plurality of image detectors attached to the gantry and radially spaced around a circumference of the bore such that gaps exist between adjacent image detectors along the circumference of the bore, an x-ray source attached to the gantry, wherein the x-ray source transmits x-rays across the bore towards at least two of the image detectors, and an adjustable source collimator interposed between the x-ray source and a center of the bore, the adjustable source collimator configured to block a portion of the x-rays produced by the x-ray source along a fan angle in a scanning direction defined by the circumference of the bore. The method includes determining positions of the image detectors relative to the x-ray source at a plurality of rotational positions of the x-ray source about the bore. The method also includes controlling the adjustable source collimator, based on the determined positions of the image detectors, to dynamically adjust a range of x-rays that are blocked by the adjustable source collimator along the fan angle during transmission of x-rays from the x-ray source as the x-ray source is rotated about the gantry relative to the image detectors and acquisition of the CT information by the at least two of the image detectors.

In accordance with an embodiment, a system is provided that includes an adjustable source collimator. The adjustable source collimator is configured to be interposed between an x-ray source and a center of a bore of a gantry of an imaging system, and is configured to block a portion of the x-rays produced by the x-ray source along a fan angle in a scanning direction defined by a circumference of the bore. The adjustable source collimator includes a plurality of openings separated by blocking portions along the fan angle.

In accordance with an embodiment, a method of acquiring computed tomography (CT) information is provided for an imaging system having a gantry having a bore extending therethrough, a plurality of image detectors attached to the gantry and radially spaced around a circumference of the bore such that gaps exist between adjacent image detectors along the circumference of the bore, an x-ray source attached to the gantry, wherein the x-ray source transmits x-rays across the bore towards at least two of the image detectors, and an adjustable source collimator interposed between the x-ray source and a center of the bore, the adjustable source collimator configured to block a portion of the x-rays produced by the x-ray source along a fan angle in a scanning direction defined by the circumference of the bore. The method includes determining positions of the image detectors relative to the x-ray source at a plurality of rotational positions of the x-ray source about the bore. The method also includes rotating the x-ray source relative to the image detectors about an object to be imaged disposed within the bore. Further, the method also includes activating the image detectors based on detector position as the x-ray source rotates about the object to be imaged to provide at least two active detectors for each rotational position. Also, the method includes controlling the adjustable source collimator, based on the determined positions of the image detectors, to dynamically adjust a range of x-rays to permit passage of x-rays to the at least two active detectors for each rotational position and to inhibit passage of x-rays that are not directed toward the at least two active detectors for each rotational position during transmission of x-rays from the x-ray source as the x-ray source is rotated about the gantry relative to the image detectors and acquisition of the CT information.

BRIEF DESCRIPTION OF THE DRAWINGS

FIG. 23A shows a schematic view of an adjustable collimator, according to an embodiment.

FIG. 23B depicts the adjustable collimator of FIG. 23A in a position corresponding to having 5 sensors within a field of view.

FIG. 23C depicts the adjustable collimator of FIG. 23A in a position corresponding to having 4 sensors within a field of view.

DETAILED DESCRIPTION

Figure 1:
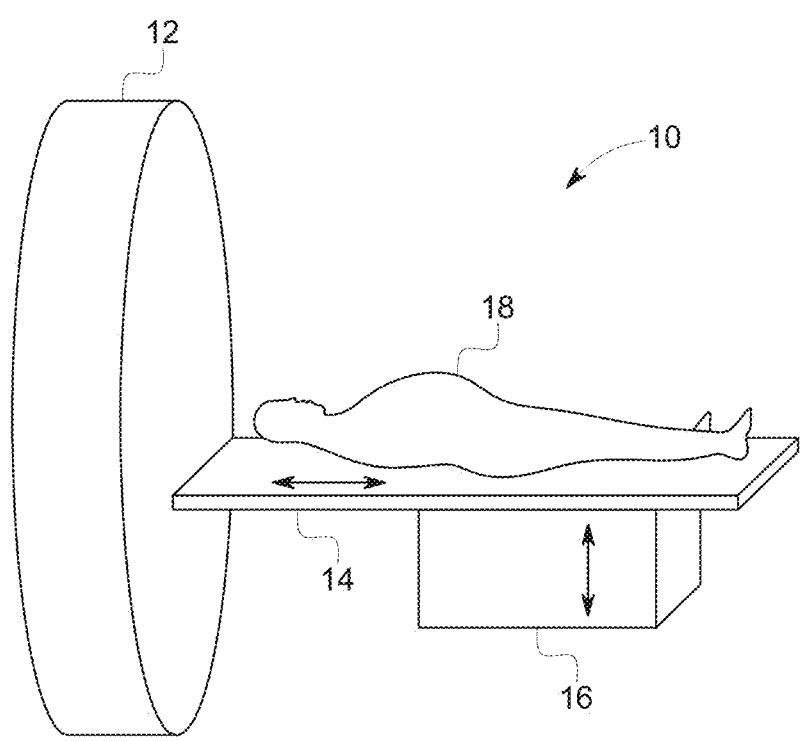
FIG. 1 shows a medical imaging system, according to an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a medical imaging system, and in particular, a Nuclear Medicine (NM) imaging system having a gantry with imaging detectors mounted thereto. For example, in various embodiments of an NM imaging system, a Single Photon Emission Computed Tomography (SPECT) imaging scanner is provided that includes a plurality of detectors with a combination of different types of detectors that acquire SPECT and CT image information. This can be done at different time intervals or simultaneously. The various embodiments may include detectors formed from different materials, having different configurations or arrangements, and/or having different collimation. The system may be configured to perform single isotope or multi-isotope imaging.

It should be noted that although the various embodiments are described in connection with a particular NM imaging system, such as a SPECT detector system, the various embodiments may be implemented in connection with other imaging systems, such as a Positron Emission Tomography (PET) imaging system.

FIG. 1 shows medical imaging system 10, according to an embodiment. Subject 18 can be a human patient in one embodiment. Alternatively, subject 18 is not human. It can be some other living creature or inanimate object in various embodiments. Subject 18 can be placed on a pallet 14 that can move a subject horizontally for locating subject 18 in the most advantageous imaging position. The bed mechanism 16 can raise and lower pallet 14 vertically for positioning subject 18 in the most advantageous imaging location. Gantry 12 is shown as circular in an embodiment. In other embodiments gantry 12 may be of any shape such as square, oval, "C" shape, or hexagonal. Gantry 12 has a bore for subject 18 to enter therein.

Figure 2:
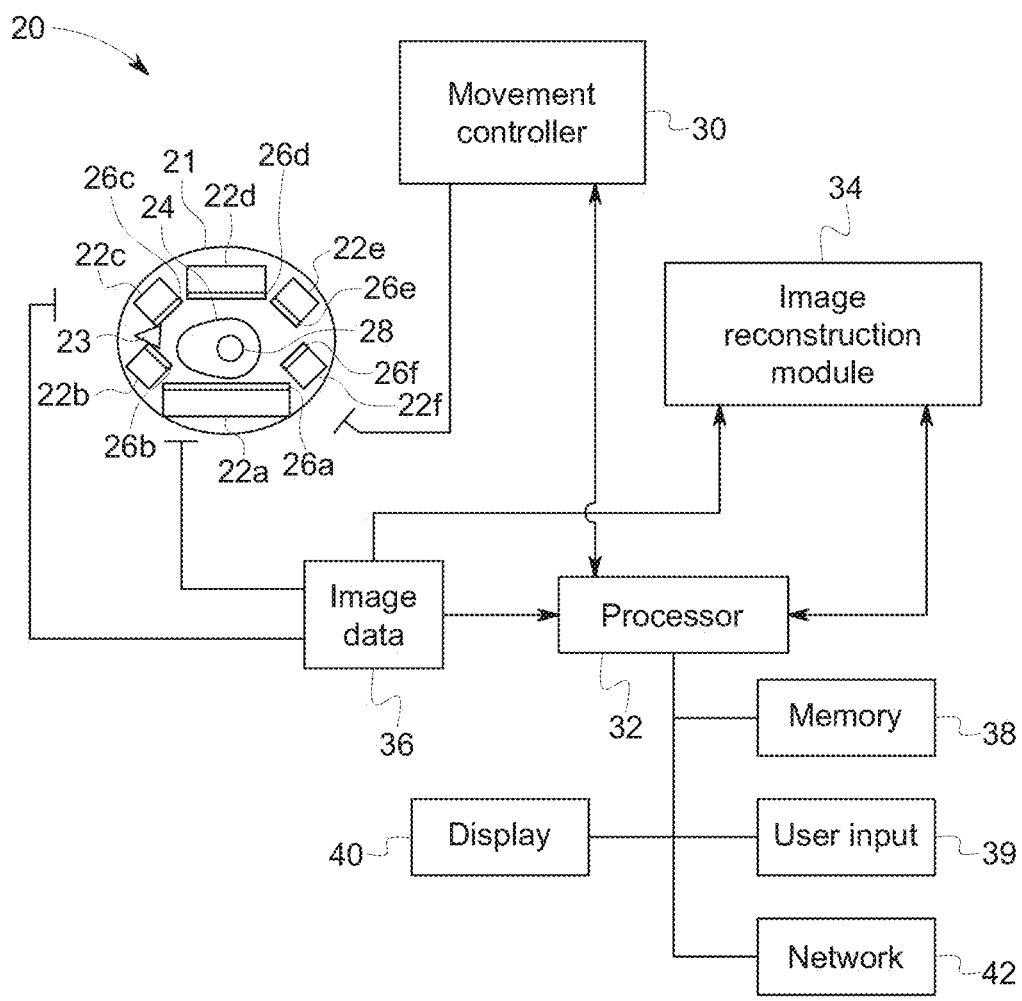
FIG. 2 shows a block diagram of a medical imaging system, according to an embodiment.

FIG. 2 shows a block chart of medical imaging system 20, according to an embodiment. A portion of patient 24 is positioned inside the bore of gantry 21. The medical imaging system 20 may be provided having a plurality of radiographic cameras configured as dual CT/SPECT detector columns 22a-22f. Detector columns 22 are attached to gantry 21, either to a stationary section of gantry 21 or its rotary member. It should be noted that the various embodiments are not limited to the medical imaging system 20 having six detector columns 22 as shown or to the sizes or shapes of the illustrated detector columns 22. For example, the medical imaging system 20 may include more or less detector columns 22 having different shapes and/or sizes, or formed from different materials. Detector columns can be called detector units in some embodiments. X-ray source (e.g. an x-ray tube) 23 is also attached to gantry 21, either to a stationary section or the gantry's rotary member. X-ray source can transmit both low-power and high-power x-ray's towards patient 24. X-ray source can transmit both low-flux and high-flux x-ray's towards patient 24.

In operation, a subject, such as patient 24, is positioned in proximity to the one or more of detector columns 22 for imaging. The imaging system 20 can then re-adjust the detector columns 22 to retract further from or extend closer to patient 24 or patient region of interest (ROI) 28 as needed, which is a heart in an example embodiment. Imaging of patient 24 is performed by one or more of detector columns 22. The imaging is performed based on x-ray transmission data, originating from x-ray source 23, and based on emission data caused by a radiopharmaceutical tracer inside patient 24. The imaging by each of the detector columns 22 may be performed simultaneously, concurrently, or sequentially.

The position of the detector columns 22 may be varied, including the relative position between detector columns 22, the tilt, the angle, the swivel, and other characteristics of the detector columns 22. Additionally, each of the detector columns 22 may have a corresponding collimator 26a-26f mounted or coupled thereto. The collimators 26a-26f likewise may be of different types. One or more detector columns 22 may be coupled to a different type of collimator 26 (e.g., parallel hole, pin-hole, fan-beam, cone-beam, etc.). Accordingly, in various embodiments, the detector column 22 wholly includes collimator 26.

The detector columns 22 may include single crystal, or multi-crystal, detectors or pixelated detectors or scintillator based detectors that are configured to acquire SPECT and CT image data. These may be referred to as detector elements. For example, the detector columns 22 may have detector elements formed from different materials, such as semiconductor materials, including Cadmium Zinc Telluride (CdZnTe), often referred to as CZT, Cadmium Telluride (CdTe), and Silicon (Si), among others, or non-semiconductor scintillator materials such as different types of crystal scintillators, for example, Sodium Iodide (NaI), Bismuth Germanate (BGO), Cerium-doped Lutetium Yttrium Orthosilicate (LYSO), Gadolinium Oxyorthosilicate (GSO), Cesium Iodide (CsI), Lanthanum(III) bromide ($LaBr_3$), among others. Additionally suitable components may be provided. For example, the detector columns 22 may be coupled to photosensors, such as an array of Photo-Multiplier Tubes (PMTs), an Avalanche Photodiode Detector (AFD), etc. Additionally, PET image data can be acquired in some embodiments. The detector elements are photon counting detectors in some embodiments. The detector elements are direct conversion or solid state in some embodiments.

Variations and modifications to the various embodiments are contemplated. For example, in a multi-headed system, namely a system having two or more detector columns 22, each detector column 22 may be formed from different materials and have different collimators 26. Accordingly, in at least one embodiment, one detector combination may be configured to obtain information for an entire field of view (FOV) while another detector combination is configured to focus on a smaller region of interest (ROI) to provide higher quality information (e.g., more accurate photon counting). Additionally, information acquired by one detector combination may be used to adjust the position, orientation, etc. of at least one other detector combination during imaging.

Imaging system 20 can also include a movement controller 30 that operates to control the movement of the x-ray source 23, detector columns 22 and/or other moving parts in gantry 21, such as its rotary member. For example, the movement controller 30 may control movement of the detector columns 22, such as to rotate or orbit the detector columns 22 around a patient 24, and which may also include moving the detectors closer to or further from the patient 24 and pivoting/swiveling the detector columns 22, such that localized movements or motions are provided. Detector controller 30 additionally may control the orbital rotation of detector columns 22 around the edges of the gantry bore, such that detector columns 22 are at a new angle to patient 24 than previously. In various embodiments, the movement controller 30 may be a single unit or multiple units controlling each separate apparatus.

The imaging system 20 also includes image reconstruction module 34 configured to generate images from acquired image data 36 received from the detector columns 22. For example, image reconstruction module 34 may operate using NM image reconstruction techniques to generate SPECT images of the patient 24, which may include an ROI 28, such as the heart of a patient. The image reconstruction techniques may be determined based on the installation status of detector column 22 acquiring the image data 36 and sending to image reconstruction module 34 and/or processor 32.

Image reconstruction module 34 may be implemented in connection with movement controller 30 and/or processor 32. Optionally, the image reconstruction module 34 may be implemented as a module or device that is coupled to or installed in the movement controller 30 and/or processor 32. Each processing module may be a separate hardware module or software module, or combined together into one chip or module in various embodiments.

CT and/or SPECT image data 36 is received by the processor 32 and/or image reconstruction module 34 may be stored for a short term (e.g., during processing) or for a long term (e.g., for later offline retrieval) in a memory 38. The memory 38 may be any type of data storage device, which may also store databases of information. Memory 38 may be separate from or form part of the processor 32. User input 39, which may include a user interface selection device, such as a computer mouse, voice activation, trackball and/or keyboard is also provided to receive a user input. User input 39 may direct processor 32 to send a movement control signal to movement controller 30 for alteration of detector column 22 and/or x-ray source 23 arrangements in the gantry. Optionally, user input 39 may be considered by the processor 32 as a suggestion and the processor 32 may choose to not execute the suggestion based on criteria.

Thus, during operation, the output from the detector columns 22, which may include image data 36, such as projection data from a plurality of detector/gantry angles is transmitted to processor 32 and image reconstruction module 34 for reconstruction and formation of one or more images. The reconstructed images and other user output can be transmitted to a display 40 such as a computer monitor or printer output. The reconstructed images and other user output can also be transmitted to a remote computing device via network 42.

Figure 3:
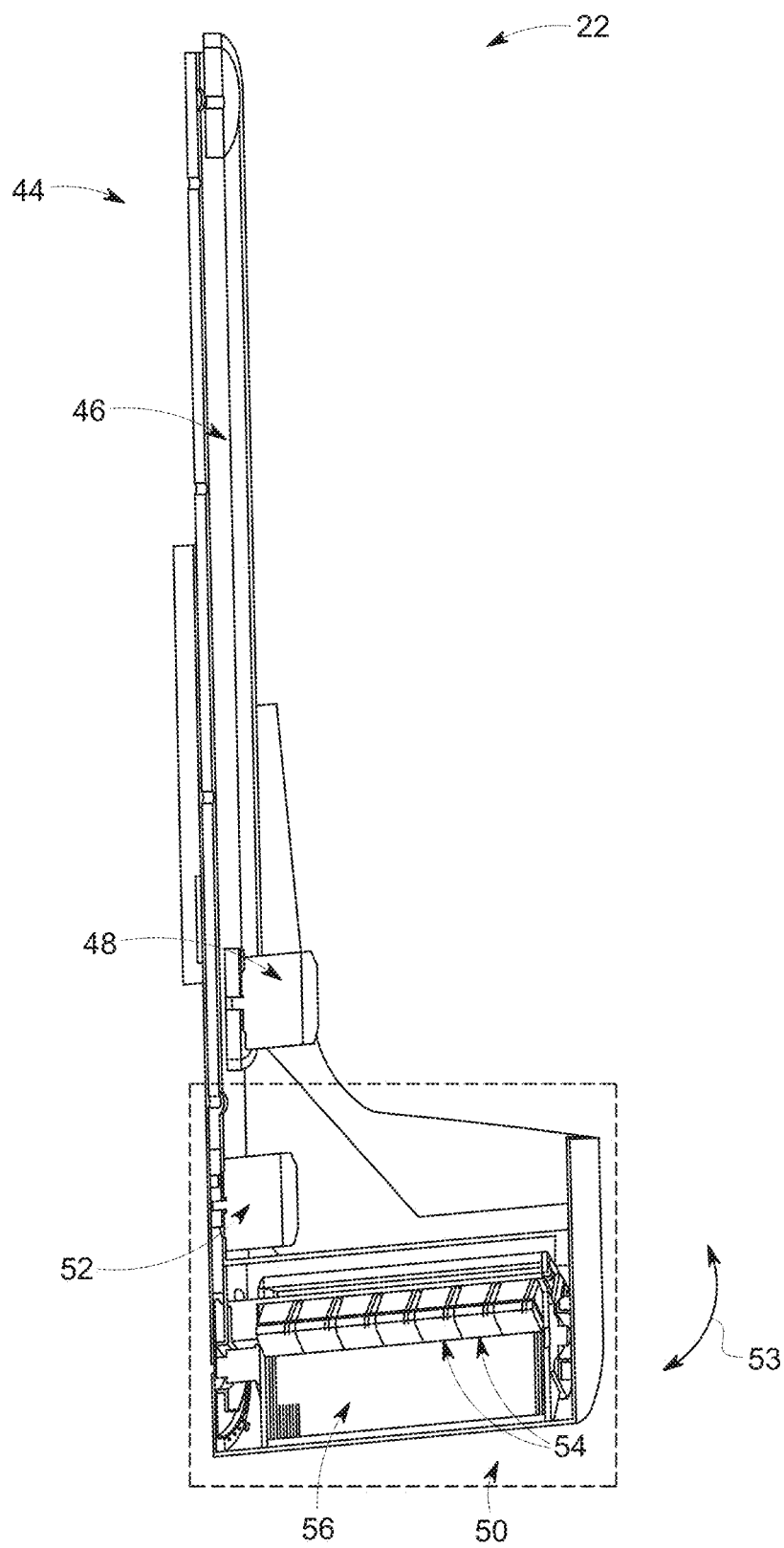
FIG. 3 shows an implementation of a detector column, according to an embodiment.

FIG. 3 shows an implementation of detector column 22, according to an embodiment. Column arm 44 attaches to a gantry and provides support for and includes a radial motion rail 46, radial motion motor 48, and detector head 50. Radial motion motor 48 controls the movement of detector head 50 by extending or retracting detector head 50 along radial motion rail 46. This provides customizability and flexibility to the imaging system. The detector column can include telescopic covers that allow it to extend and contract as it moves radially in and out.

The detector head 50 includes sweep motor 52, detector elements 54, and collimator 56. Detector elements 54 can be CZT modules or other detector element modules for detecting CT and SPECT image data. Sweep motor 52 controls the rotation angle of the detector head 50 in relation to the arm 44. Sweep pivoting axis 53 shows the rotation angle axis of the detector head 50. Movement controller 30 can provide instruction and control to either or both of the radial motion motor 48 and sweep motor 52. Thus, each detector column 22 is independently controllable in the radial location as well as the angle of tilt of the detector head 50. Radial motion motor 48 and sweep motor 52 can be two separate motors as shown in the embodiment of FIG. 3. Alternatively, the functionality of the two motors may be provided by one motor.

Figure 4:
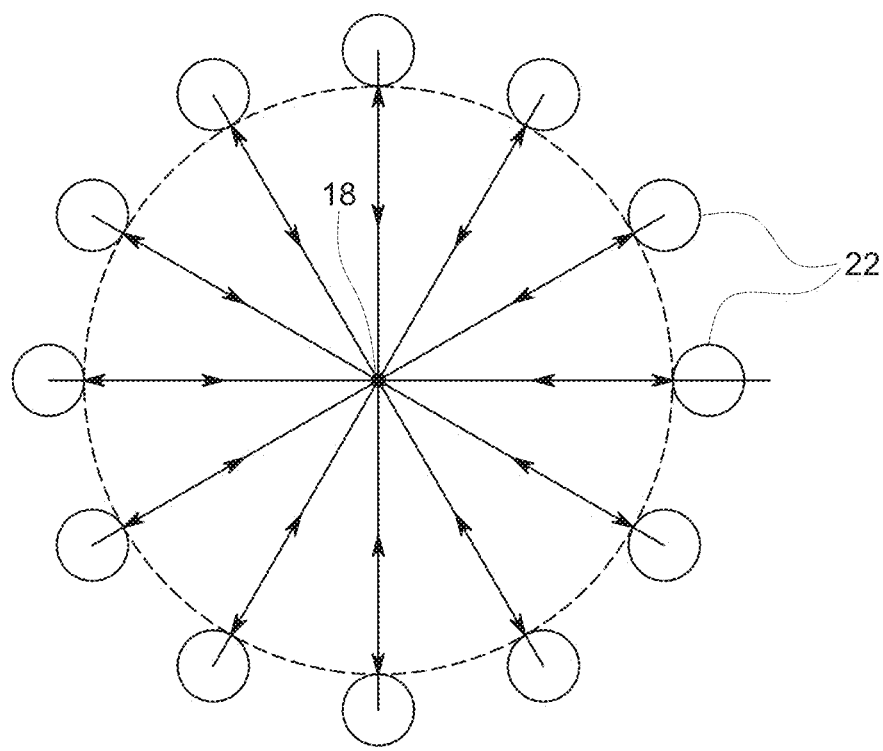
FIG. 4 shows a radial construction of an imaging system, according to an embodiment.

FIG. 4 shows a radial construction of an imaging system where twelve detector columns 22 are placed at a consistent angle, thirty degrees in this example, from each other along the circumference of a gantry bore, according to an embodiment. FIG. 4 also shows physical gaps between detector columns 22. Thus, the detector columns 22 are uniformly distributed in this example. Each detector column 22 is movable along a radial axis. This allows the detector heads on detector columns 22 to be closer or further from a subject 18 for imaging. The gap between two detector heads decreases as the detector columns are extended towards the center of the bore. The circles in the figure depict the location of detector head 50 of detector column 22. The detector columns are shown along the dotted line as their outer limit position in this view of one embodiment. The dual head radial arrows depict the in-out direction of motion of the detector columns 22.

Figure 5:
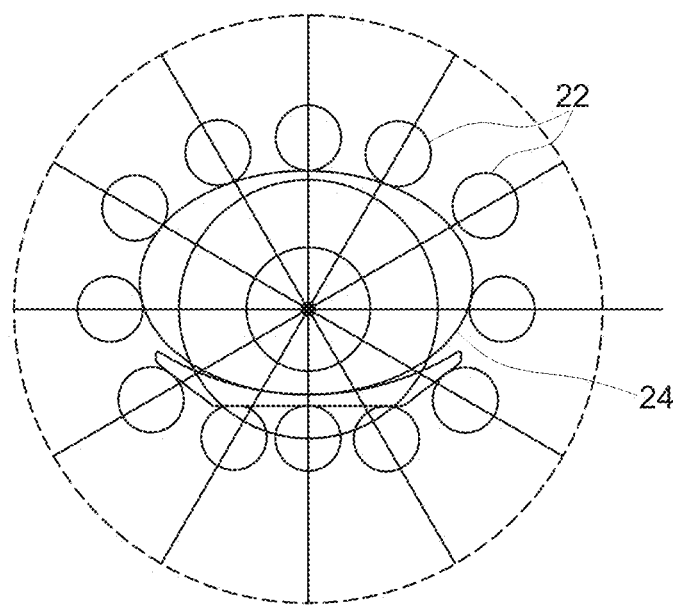
FIG. 5 shows a radial construction of an imaging system where twelve detector columns have their heads placed at a consistent angle and have been moved radially inward to be in positions close to a patient, according to an embodiment.

FIG. 5 shows a radial construction where twelve detector columns 22 have their heads placed at a consistent angle and have been moved radially inward to be in positions close to a patient 24, according to an embodiment. As FIG. 5 shows, some of the detector heads are further towards the center of their radial axis than others. This allows for high-quality imaging results with varied-sized objects. The resolution of SPECT detection can degrade as an image detector moves further from the emission source.

Figure 6:
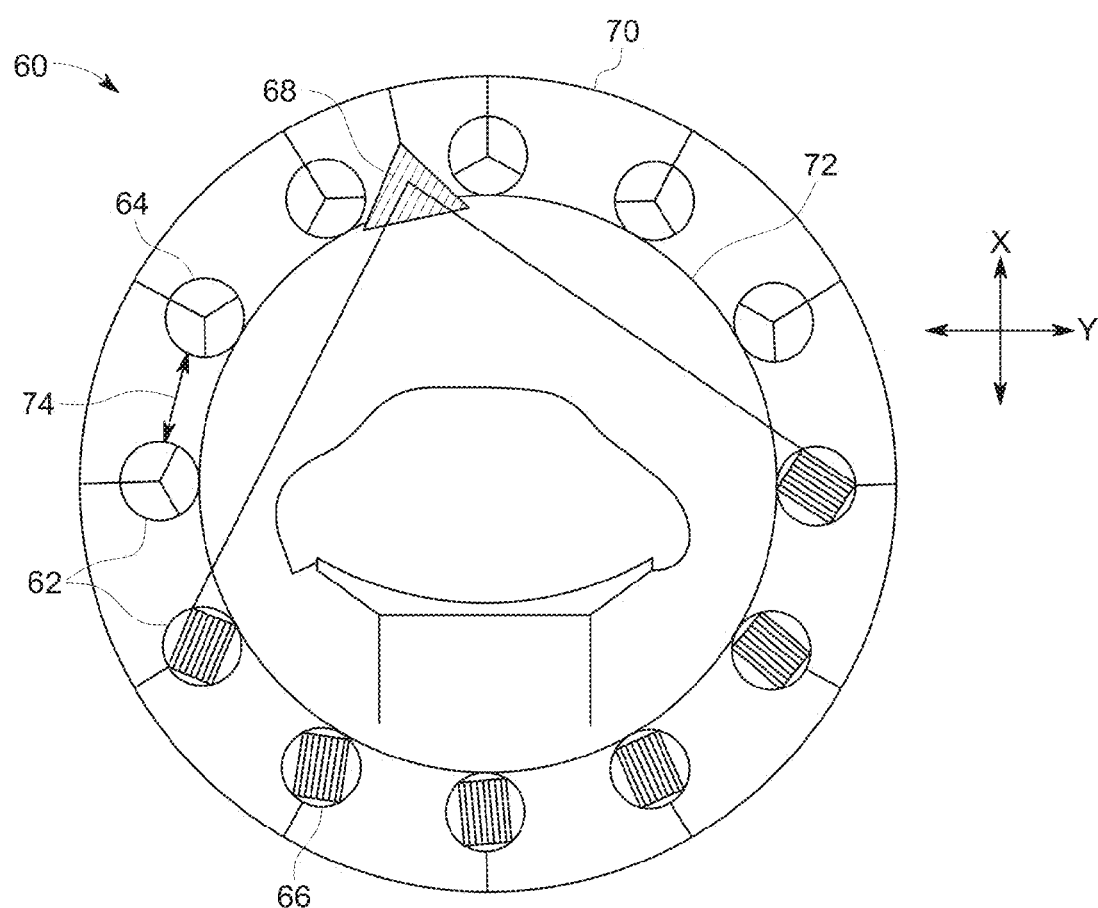
FIG. 6 shows a gantry in a medical imaging system, according to an embodiment.

FIG. 6 shows gantry 60 in a medical imaging system, according to an embodiment. Attached to gantry 60 are detector columns 62 radially spaced around a circumference of the bore, which can include active columns 66 and inactive columns 64. A space 74 exists between detector columns such that there is a gap in image detection coverage. X-ray tube 68 is also attached to gantry 60. X-ray tube 68 transmits x-ray radiation across the X-Y, or scanning, plane. FIG. 6 shows the x-ray transmission in a fan beam, according to an embodiment. Only active columns 66 that are within the fan beam are activated for image detection in one embodiment. Active columns 66 are columns currently in use to detect x-ray radiation transmitted from x-ray tube 68. Inactive columns 64 are not currently in use to detect x-ray radiation. Emission detection from an in-patient tracer can be detected from active column or an inactive column, as active and inactive in this context refer to x-ray radiation detection.

FIG. 6 also shows the detector heads of active columns 66 angled to be pointing towards x-ray tube 68 to achieve the best image quality. Active columns 66 can point towards the x-ray tube focal spot in an embodiment. Sweep motor 52 angles the detector heads towards x-ray tube 68 if the detector column 62 is in the active zone of the x-ray transmission and can return the detector head angle to a standard position or angled at an emission ROI if the detector column 62 is not in the active zone of the x-ray transmission.

Detector columns 62 may be attached to the gantry via a rotary member 70 or a stationary structure. Detector columns 62 may be regularly spaced around the circumference of the bore as shown by example in FIG. 6 or irregularly spaced around the circumference of the bore as shown by example in FIG. 2. X-ray tube 68 may be attached to the gantry via a rotary member 70 or a stationary structure. In some embodiments both detector columns 62 and x-ray tube 68 are attached to the gantry via a rotary member 70. Rotary member 70 is annular in an embodiment. Annular member 72 can be part of rotary member 70 in one embodiment. Annular member 72 can be a second rotary member as discussed further below with regard to FIG. 7.

Figure 7:
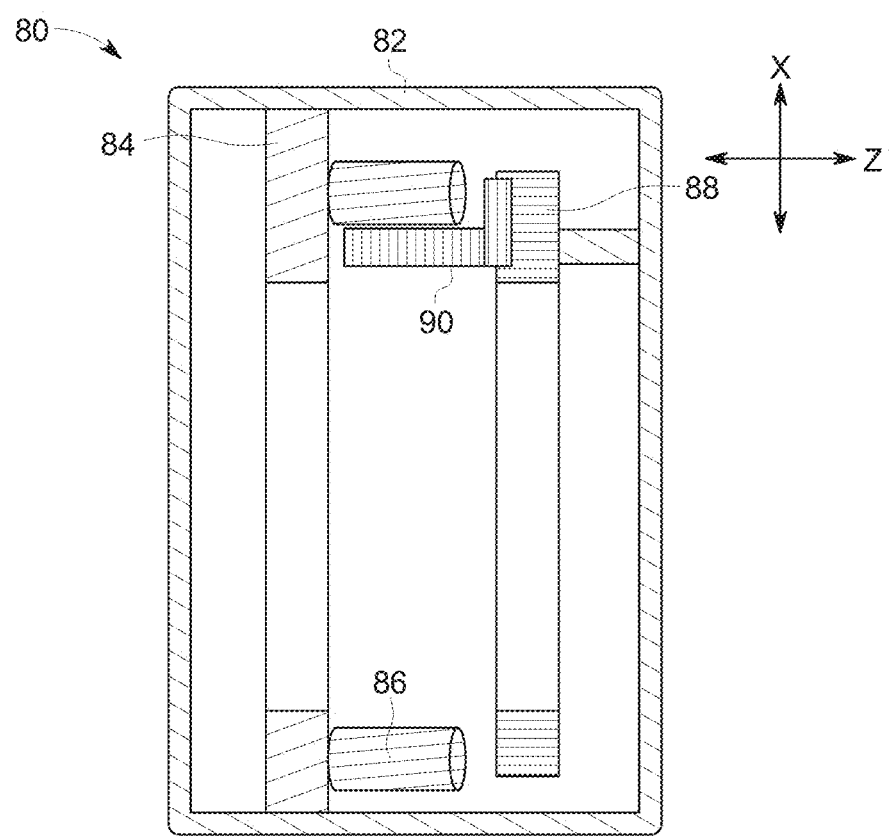
FIG. 7 shows a side view of a gantry in an imaging system, according to an embodiment.

FIG. 7 shows a side view of gantry 80 in an imaging system, according to an embodiment. A patient can be positioned into the gantry bore along the z-axis for medical imaging as shown in FIG. 1. Stationary structure 82 provides a housing and support for the system. First rotary member 84 is attached to stationary structure 82 with detector columns 86 attached to it. Second rotary member 88 is attached to stationary structure 82 with x-ray tube 90 attached to it. FIG. 7 shows that x-ray tube 90 can rotate in an orbit around the center of the bore along an inner circumference, while detector columns 86 can orbit around the center of the bore along an outer circumference. This prevents any collision of elements and any occlusion of the x-ray transmission by detector columns on the same side of the bore. In alternative embodiments, one of the two rotary members can be stationary, fixed to the gantry. In an alternative embodiment, the x-ray tube is attached to the same rotary member as the detector columns, discussed further below.

In an embodiment, x-ray tube 90 is moved in the Z-direction out of the X-Y plane of the imaging detectors when not in use. This allows for full extension and retraction of detector columns 86 during an NM imaging phase. In an alternate embodiment, x-ray tube 90 can be rotated orbitally by second rotary member 88 to a position that is between two detector columns 86, also allowing full extension and retraction of detector columns 86 during an NM imaging phase.

Figure 8:
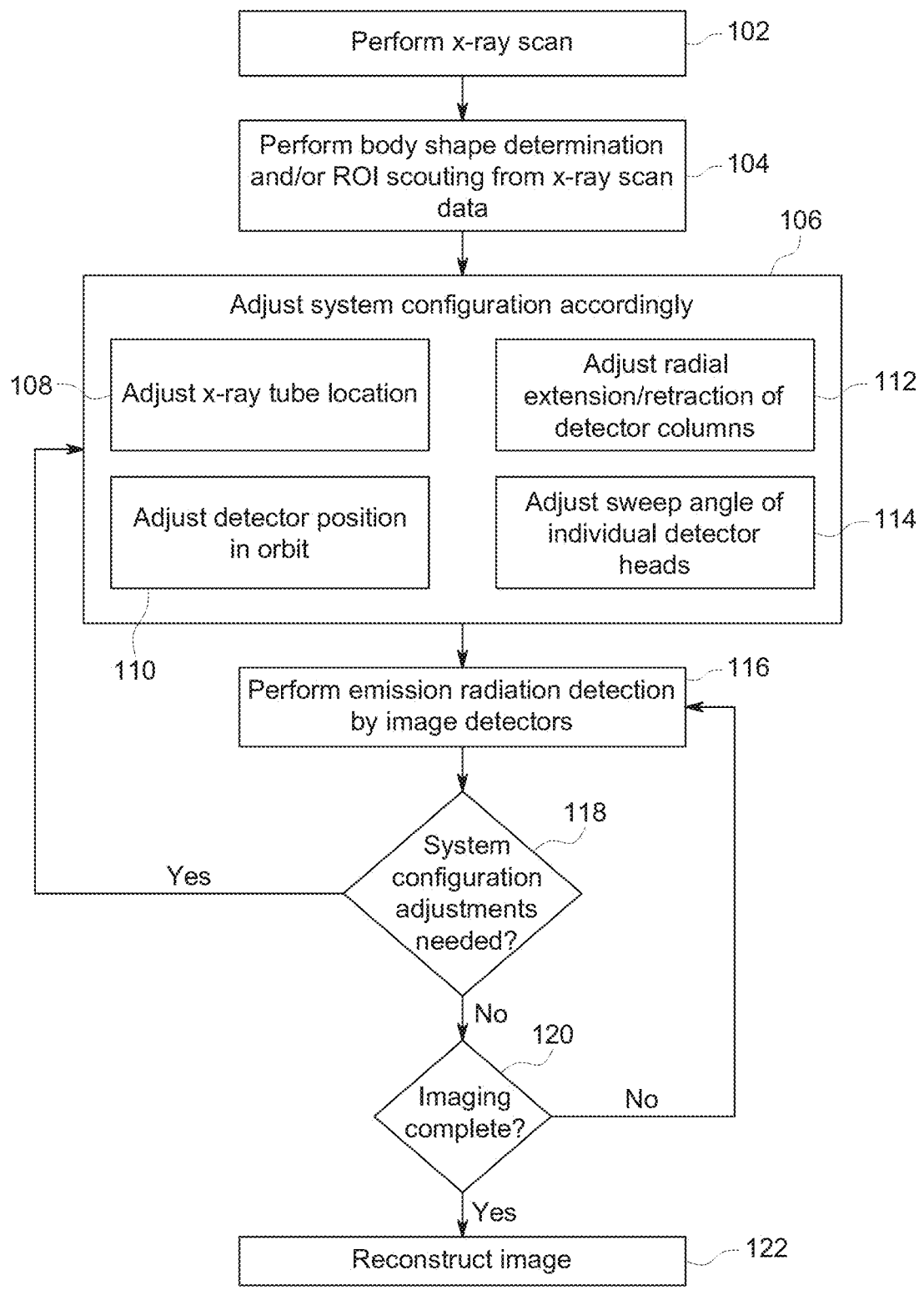
FIG. 8 shows the steps of an imaging operation using both x-ray and emission data, according to an embodiment.

FIG. 8 shows the steps of an imaging operation detecting both x-ray and emission data, according to an embodiment. The imaging system can use x-ray data to derive CT information to assist in body shape determination and/or ROI scouting. This allows the NM imaging operation to be performed with higher accuracy and performance by allowing the detector columns to focus on the correct aspects of the patient. The detector columns thus have helpful information to extend or retract at appropriate times. The sweep motors can determine what angles the detector heads should be positioned. And the rotary member supporting the detector columns has information on when it should rotate for maximum imaging. This process may be called planned focused acquisition. It includes the ability to plan the positioning and motion of the detectors to focus the attention of the detector on the target zones. This can save acquisition time, reduces risk of patient movement, increase patient comfort, and the useful output of the image detector.

In step 102, the system performs an x-ray scan, which is discussed further throughout. In step 104, the x-ray scan data is converted to CT data for determining body shape information and/or region of interest scouting. Body outer shape determination helps the system plan the NM imaging acquisition and helps avoid collisions of the detector heads with the body in such system with extendable and retractable detector columns. Scouting the organs of interest to be imaged in the body helps the system focus on the correct locations for best image quality of the organ. The system can also thus detect which detector columns (if the detector columns are not all the same) may be best for the specific scan. This can be in a situation where some detector columns have higher quality materials or materials specifically tailored to the needs of the scan to be performed. The scan to be performed can depend on the type of scan and scan protocol selected by a user or the system based on some criteria. The selections can be communicated across a computer network to the imaging system.

In step 106, the imaging system, through electronics, processor, and computer code, adjusts the system configuration according to the information developed in step 104 or step 118. The adjustments can include, but are not limited to, the actions in steps 108-114. In step 108, the system adjusts the x-ray tube location, either radially around the circumference of the bore, or in the Z-direction. This can be to continue an x-ray acquisition or to position the x-ray tube in a standby location. In step 110, the system adjusts the orbital location of one or more detector columns radially around the circumference of the bore. In step 112, the system extends or retracts one or more independently movable detector columns. In step 114, the system adjusts the sweep angle of one or more of the independently controllable detector heads by use of the sweep motors. These steps are generally done to improve NM or CT imaging. While not shown in FIG. 8, the system may also adjust the position of the table supporting the patient in step 106, in the X, Y, and/or Z directions.

In step 116, the system performs NM imaging by detecting emission data from within a subject or patient. Some or all of the detector columns may be activated for step 116. In step 118, the system determines if hardware configuration adjustments are needed, as done by step 106. If YES, the system returns to step 106 for one or more system reconfiguration actions to be completed. If NO, the system moves to step 120. In step 120, the system determines if the imaging operation is complete. If NO, additional data is collected at step 116. If YES, the system moves to step 122. In step 122, the system reconstructs the image. The reconstruction can be done from just the emission data, or the emission and x-ray data in conjunction. This reconstruction can be done through iterative reconstruction or other techniques known in the art of medical imaging. The reconstructed image is then stored in a computer memory and/or displayed on a screen to a user, according to an embodiment.

Figure 9:
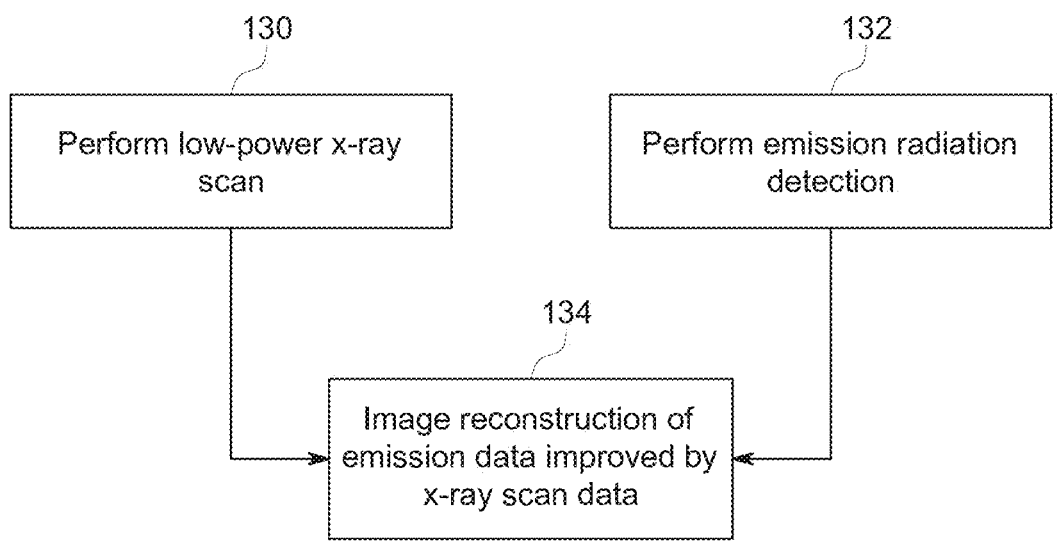
FIG. 9 shows the steps of a concurrent imaging operation, according to an embodiment.

FIG. 9 shows the steps of a concurrent imaging operation, according to an embodiment. In step 130, the system performs an x-ray scan by instructing the x-ray tube to transmit x-rays through the gantry bore towards one or more detector columns. As discussed further herein, the active detector columns in the fan beam of the x-ray transmission can angle their detector heads to point towards the x-ray tube. The x-ray scan can be low power or flux according to one embodiment. This allows certain materials, such as some CZT configurations, to be used for simultaneous acquisition of both x-ray and gamma ray (emission) data. Low power x-ray transmissions are generally below one kilowatt, according to one embodiment. Low power x-ray transmissions can be as low as one to twenty-five watts, according to one embodiment. In other configurations, the system may best perform with high power or flux x-ray transmissions. High power may be over ten or twenty kilowatts, according to one embodiment.

In step 132, simultaneous emission radiation detection occurs. Step 130 or 132 may be longer than the other, but simultaneous here means that they occur in overlapping time periods. The detector columns are dual use, according to an embodiment. As shown in FIG. 6, inactive columns 64 can be in a NM detection only mode. If x-ray tube 68 moves around the circumference of the gantry such that the fan beam includes an inactive column 64, the system can change the column into an active column 66, which can operate in a dual acquisition mode. In such a dual acquisition mode, the detector column can acquire both x-ray and emission information and separate the two with photon counting modes, energy windowing for tissue type discrimination, or other techniques known in the art. Emission data can be subtracted and filtered by energy values, according to an embodiment.

In step 134, an image reconstruction is done of the emission data acquired in step 132. The image reconstruction is improved by incorporating some of the results from the x-ray scan data from 130. Such improvements can be attenuation correction, localization of NM findings in relation to body organs, and cross registration to the diagnostic anatomical image from the x-ray data. As a consequence of attenuation, quantitative image values in the various projections do not accurately represent line integrals of the radioisotope distribution within the body. It is therefore necessary to correct for this distortion. If the emission data is to be corrected for attenuation, x-ray transmission data must be acquired at each station. Thus, attenuation correction provides a computer map of the density of the patient to correct the emission data. The attenuation computer map and emission data can be used for creation of an attenuation corrected isotope distribution image, without ever creating a non-corrected image, according to an embodiment.

The steps of FIG. 9 may include the system configuration adjustments of step 106, according to an embodiment.

Figure 10:
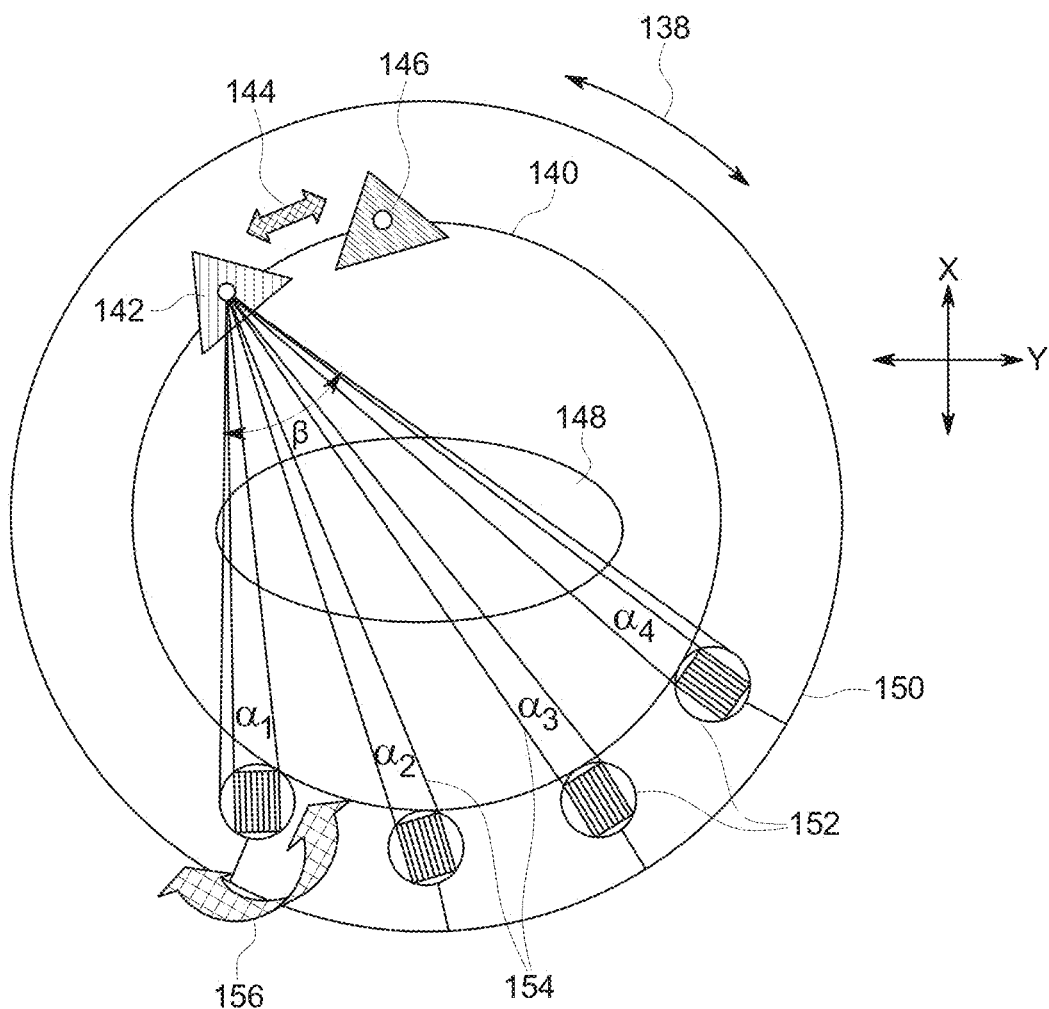
FIG. 10 shows a cross section of a gantry during an image scan, according to an embodiment.

FIG. 10 shows a cross section of a gantry during an image scan, according to an embodiment. Rotary member 140 is attached to a gantry and orbits along the outside of the bore, as indicated by arrow 138, along an inner circumference. Rotary member 140 is annular in an embodiment. X-ray tube 142 is attached to rotary member 140. X-ray arrow 144 shows the movement of the x-ray tube as the rotary member rotates. X-ray tube position 146 shows the position of the x-ray tube 142 after it has been rotated around the bore a certain distance.

X-ray tube 142 transmits x-rays that pass through subject 148 towards image detectors 152. Image detectors 152 are attached to stationary structure 150. Thus, in this embodiment, only one rotary member is included in the imaging system. This can save money compared to a two rotary member embodiment. Image detectors 152 can adjust their sweep motion 156 so they are pointing towards x-ray tube 142 as it moves to different positions, such as x-ray tube position 146, around the circumference of the bore. Thus, image detectors 152 capture the highest intensity x-rays.

The x-ray tube transmission can be in a fan beam configuration as shown in FIG. 10. The fan beam has an angle $\beta$, which can be around 80 degrees in an embodiment. It can change based on the specific x-ray tube installed and the specific settings in the hardware and software. The angular amount of the fan beam that hits each detector is window 154 defined by angle $\alpha$. As shown in FIG. 10, the four detectors have four windows: $\alpha 1$, $\alpha 2$, $\alpha 3$, and $\alpha 4$. The total angle of coverage $\alpha 1 + \alpha 2 + \alpha 3 + \alpha 4$ is less than the total angle β of the fan beam. This defines gaps that exist between image detectors 152. The gaps shown in FIG. 10 are over fifty percent of β, according to an embodiment. In alternate embodiments the gaps may be over eighty percent or as low as ten percent. This can change based on image detector size, amount of image detectors in the system, fan beam angle, and other factors. The system must work to overcome these gaps in coverage to acquire quality x-ray image data.

In an embodiment, x-ray tube 142 can include a collimator with the ability to block x-ray transmission to areas outside of α coverage, thus reducing radiation dose to subject 148. The system can perform a method to detect the current location of the x-ray tube around the circumference of the bore. The system can then detect image detector location and angles and compare them with the tube location. The system can then activate image detectors within the beam and calculate the gap angles (inside the beam but not hitting a detector. Then the system can instruct an adaptive collimator to block transmission to the gap angles. If the relative positioning between the source and detectors is fixed, then a fixed collimator may be used that blocks gap radiation.

FIGS. 11-14 show an x-ray data scan with gaps between image detectors, according to an embodiment. These image detectors can be detector columns with sweeping detector heads as discussed above.

Figure 11:
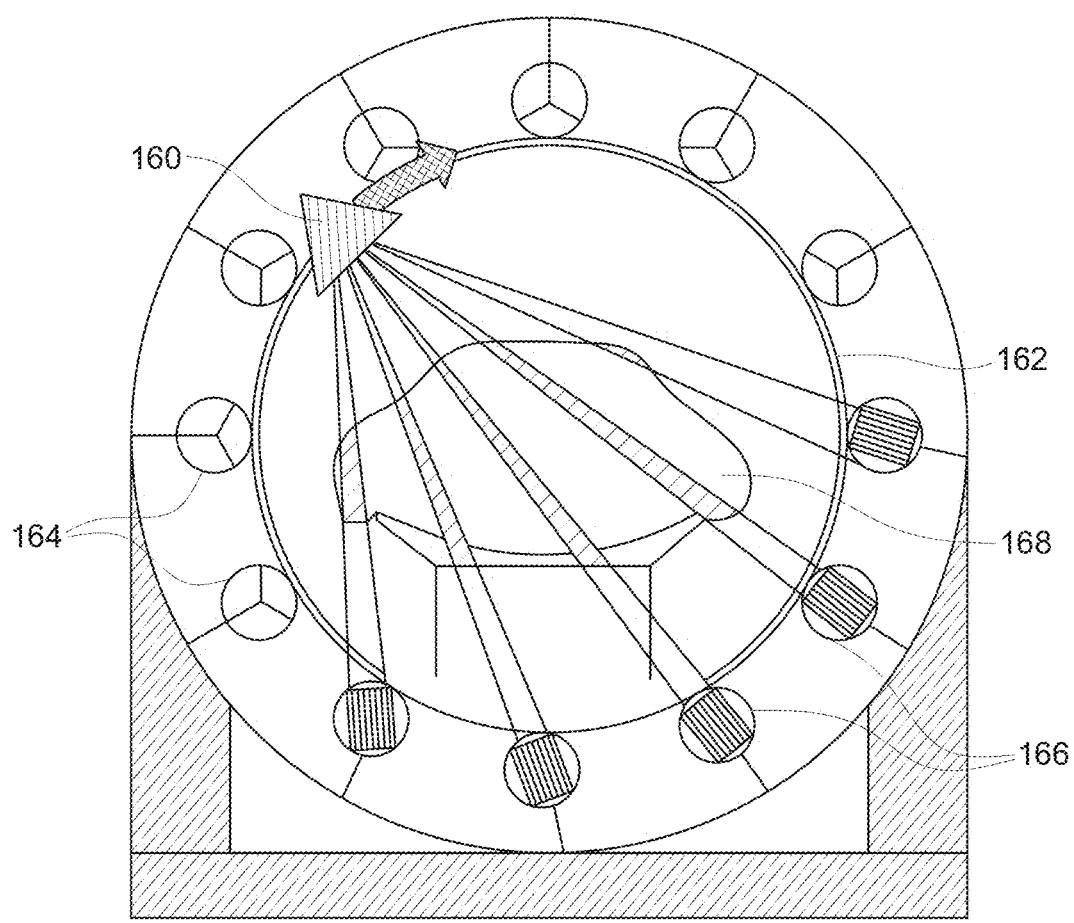
FIG. 11 shows the initial movement of an x-ray tube moving as attached to a rotating rotary member around a subject in the bore of a gantry, according to an embodiment.

FIG. 11 shows the initial movement of x-ray tube 160 moving as attached to rotating rotary member 162 around subject 168 in the bore of a gantry, according to an embodiment. Image detectors are attached around the outside of the gantry, in fixed location attached to a stationary structure of the gantry in an embodiment. Active detectors 166 are in use for the x-ray data acquisition. Inactive detectors 164 are not in use for the x-ray data acquisition. The system may also completely shut off certain detectors as the x-ray tube passes in front, occluding photon detection. This would be a blocked detector according to an embodiment. FIG. 11 shows five angles α of transmission to five active detectors 166. FIG. 11 shows the section of subject 168 that has been scanned. To address the gaps between detectors, rotary member 162 continues its orbit.

Figure 12:
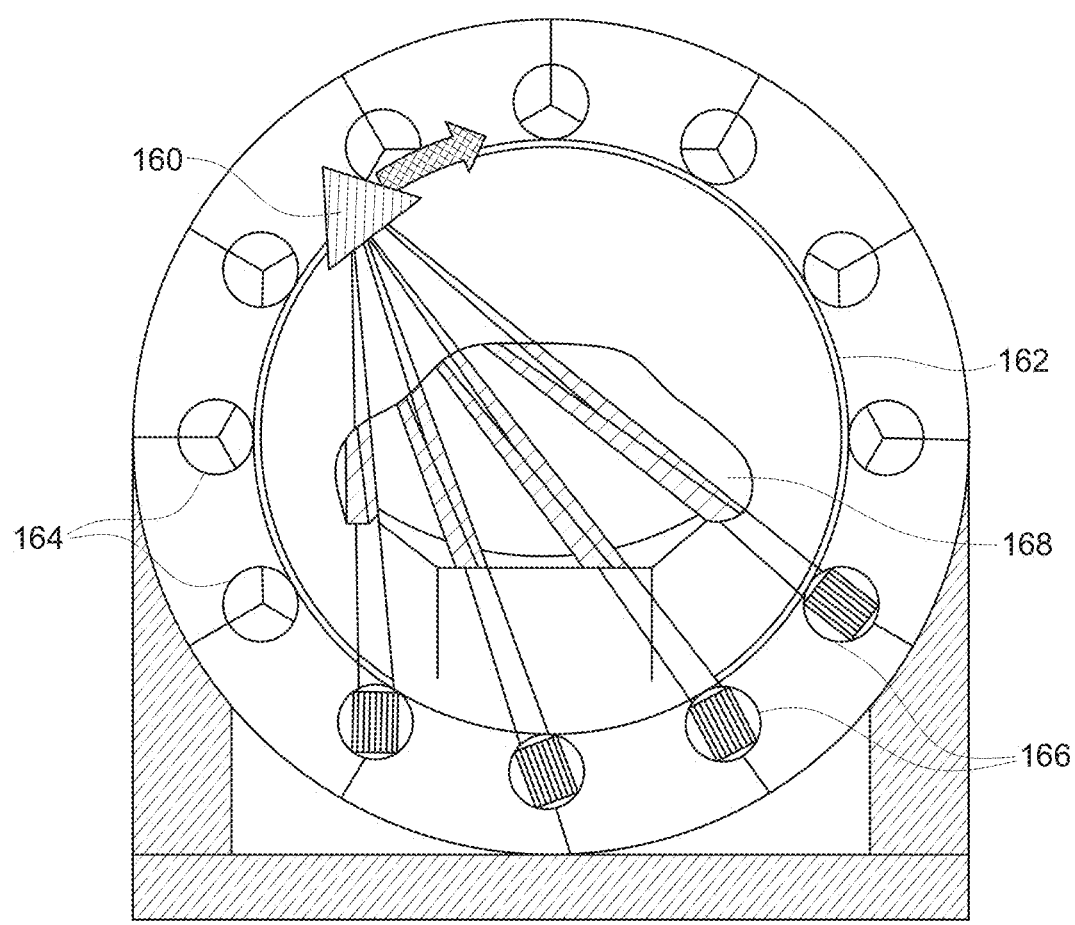
FIG. 12 shows a second movement location of an x-ray tube during an x-ray data scan, according to an embodiment.

FIG. 12 shows a second movement location of x-ray tube 160 during an x-ray data scan, according to an embodiment. Additional sections of subject 168 have been able to be scanned due to the movement. As x-ray tube 160 has moved, its transmission beam has also moved. Thus, FIG. 12 shows only four angles α of transmission to four active detectors 166. The right-most detector, an active detector in FIG. 11, has become an inactive detector 164.

Figure 13:
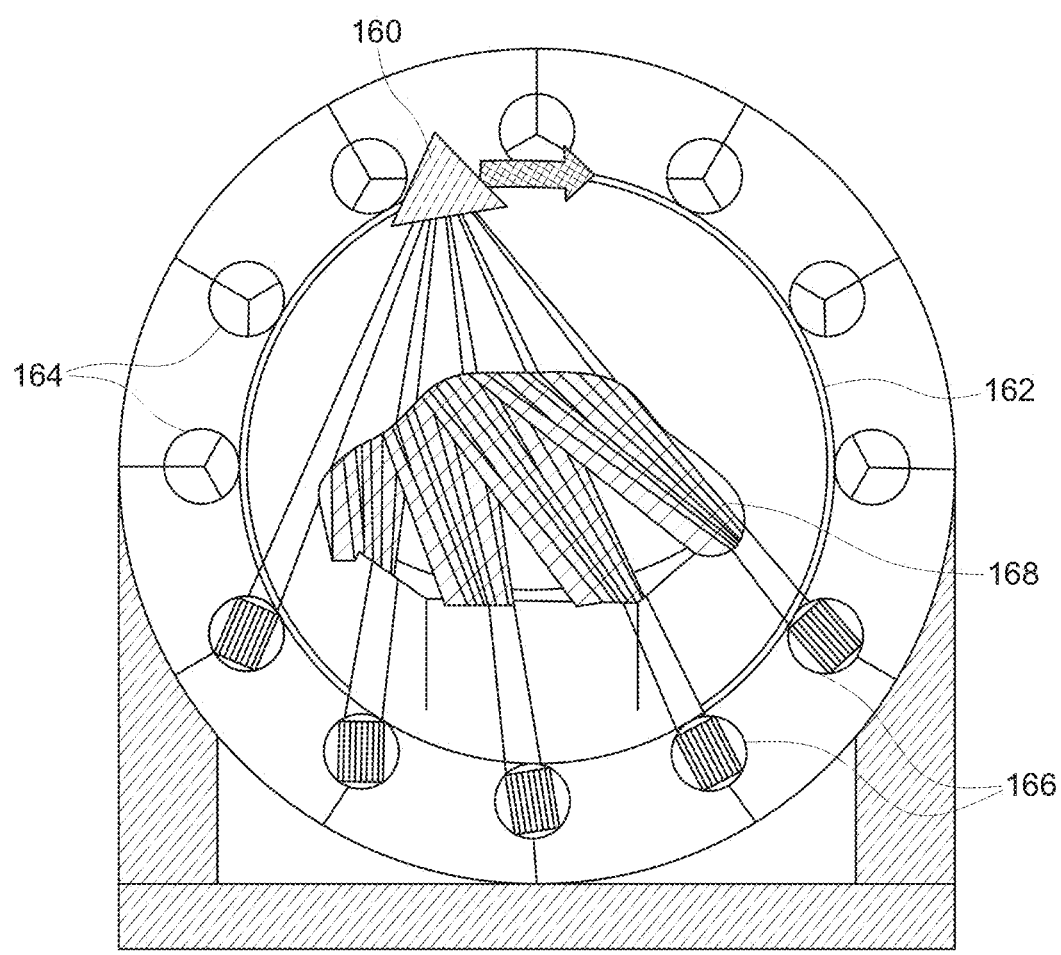
FIG. 13 shows a seventh movement location of an x-ray tube during an x-ray data scan, according to an embodiment.

FIG. 13 shows a seventh movement location of x-ray tube 160 during an x-ray data scan, according to an embodiment. Additional sections of subject 168 have been able to be scanned due to the movement. As x-ray tube 160 has moved, its transmission beam has also moved. Thus, FIG. 13 shows five angles α of transmission to five active detectors 166. Another detector on the lower left has become an active detector 166.

Figure 14:
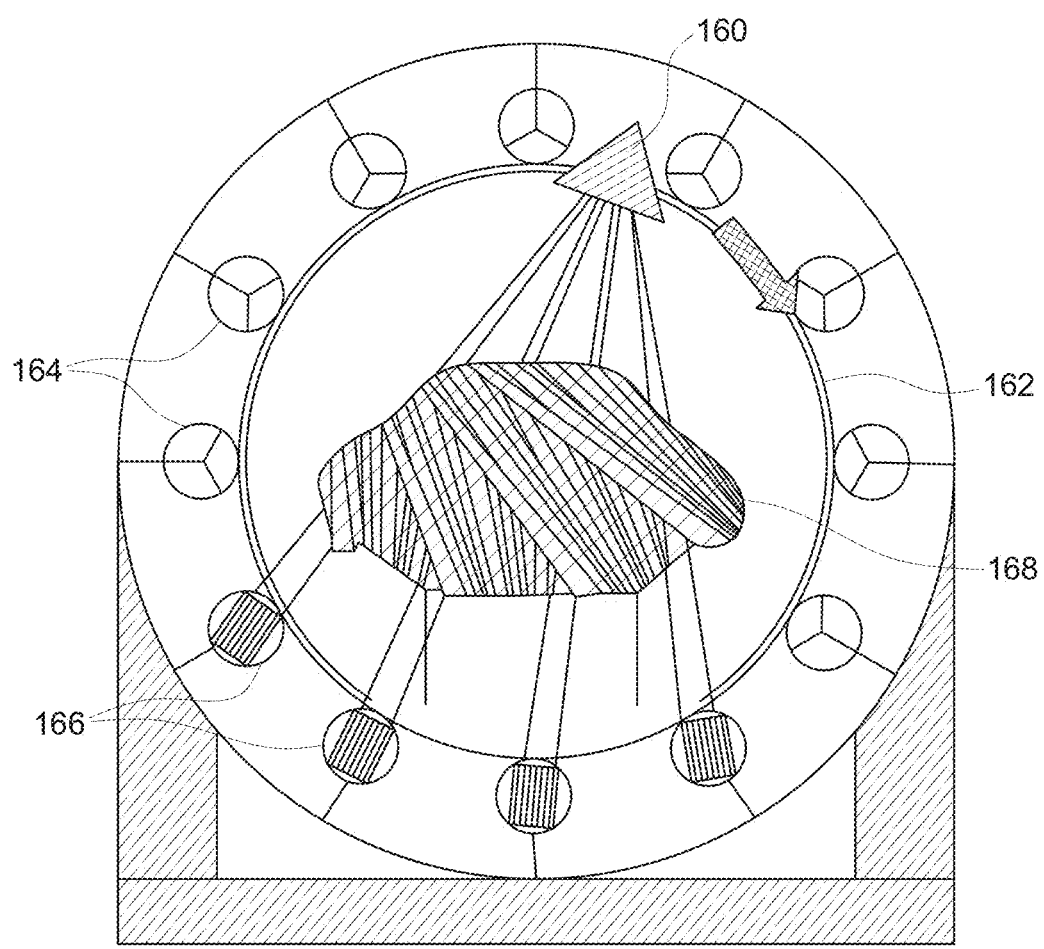
FIG. 14 shows a final movement location of an x-ray tube during an x-ray data scan, according to an embodiment.

FIG. 14 shows a final movement location of x-ray tube 160 during an x-ray data scan, according to an embodiment. Additional sections of subject 168 have been able to be scanned due to the movement. As x-ray tube 160 has moved, its transmission beam has also moved. Thus, FIG. 14 shows four angles α of transmission to four active detectors 166. Another detector on the lower right has become an inactive detector 164. Subject 168 has had almost all areas of the X-Y cross section in the bore scanned with the x-ray tube not completing a full revolution around the circumference of the bore. A quick scan such as shown can give low quality data to assist with simultaneous or future emission (such as PET or SPECT or NM) imaging. It should be noted that FIG. 14 shows that the detector heads have continued to be angled towards x-ray tube 160 as it has moved around the circumference of the bore. For applications such as attenuation correction, 180 degrees or 360 degrees single revolution of x-ray tube 160 may be enough. Thus, an adequate CT image can be made from the x-ray scan data, even when 20% total angle α coverage. In other applications, the system may run a helical scan by including movement of the table as part of the x-ray scan data. The height of the bed/pallet may also be adjusted to improve image quality. Additional ways to improve the x-ray scan coverage and CT image results are discussed herein.

Figure 15:
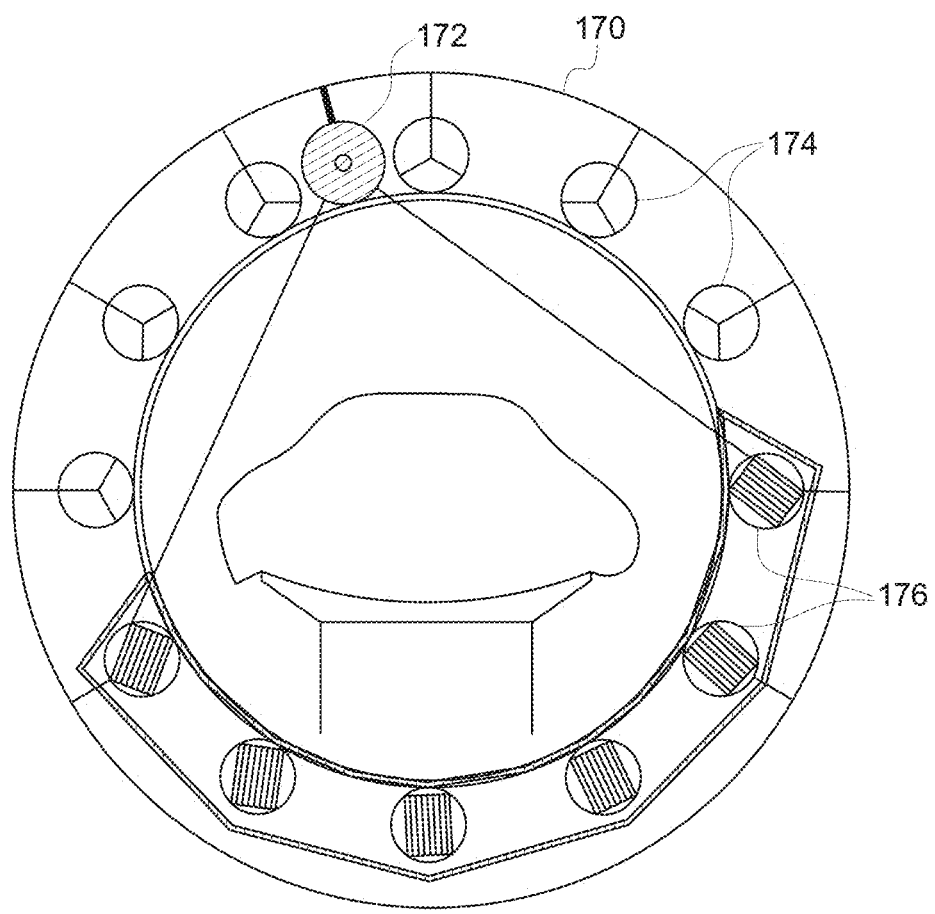
FIG. 15 shows an imaging system with a single rotary member attached to a gantry, according to an embodiment.

FIG. 15 shows an imaging system with a single rotary member 170 attached to a gantry, according to an embodiment. X-ray tube 172, emission detectors 174, and dual detectors 176 are all attached to rotary member 170. X-ray tube 172 is attached to rotary member 170 between the installations of two emission detectors 174. Thus, only a portion of the image detectors in the system, dual detectors 176, need to be able to handle x-ray transmission data. FIG. 15 shows six dual detectors 176 and six emission detectors 174, according to an embodiment. Thus, the system can include emission-only detectors. These can be preferred in some embodiments as they can be less expensive or faster in image transmission. Rotary member 170 rotates orbitally around a subject and moves X-ray tube 172, emission detectors 174, and dual detectors 176 along with it to perform x-ray scan imaging. Dual detectors 176 always have the same detector head angle towards x-ray tube 172 in this embodiment. Sweep motors thus may be not needed for dual detectors 176 then in this case, saving cost and complexity. This embodiment can be less expensive, lighter, and simpler to produce and maintain. Alternatively, a detector column can be removed from the system and the x-ray tube placed in its location. This is helpful in circumstances where the x-ray tube is large.

Figure 16:
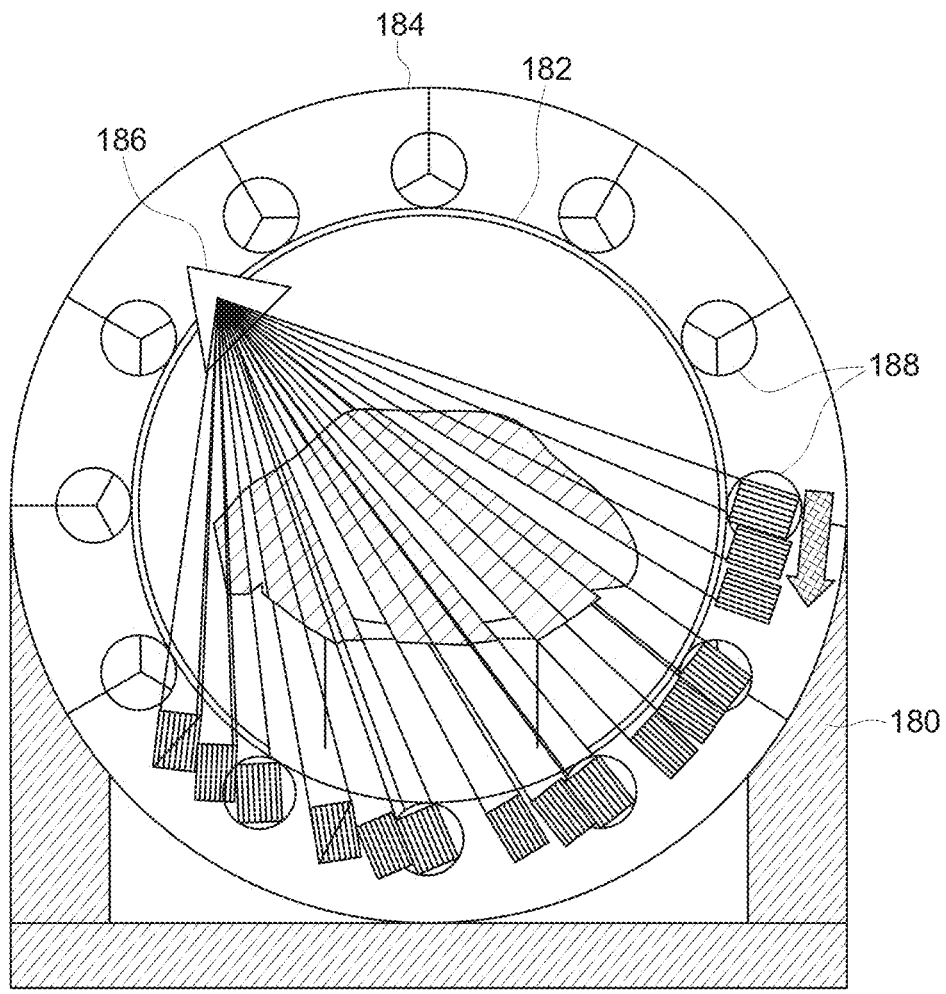
FIG. 16 shows an imaging system with image detectors attached to a rotary member, according to an embodiment.

FIG. 16 shows an imaging system with image detectors 188 attached to a rotary member 184, according to an embodiment. Rotary member 184 may perform a 360 degree or less rotation. X-ray tube 186 is attached to stationary structure 182, which is part of gantry 180. In this embodiment, x-ray tube 186 is stationary and the image detectors 188 are rotated orbitally around the circumference of the bore by rotary member 184. FIG. 16 shows the detector head angles adjusting to be pointing towards x-ray tube 186 as the image detectors 188 revolve around the gantry.

Figure 17:
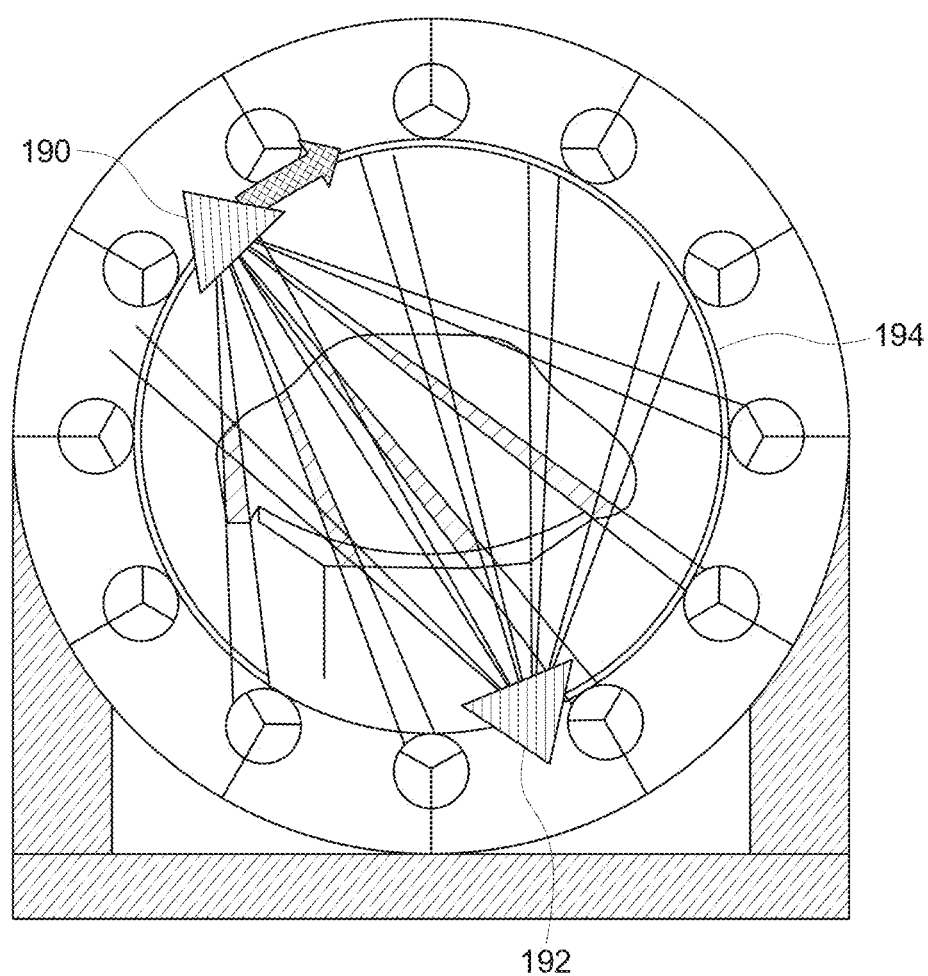
FIG. 17 shows an imaging system with multiple x-ray tubes, according to an embodiment.

FIG. 17 shows an imaging system with multiple x-ray tubes, according to an embodiment. First x-ray tube 190 and second x-ray tube 192 are attached to rotary member 194. Image detectors in the system detect the x-ray data to reconstruct CT images and correct/enhance NM images. The x-ray tubes may be set at the same or varying power levels. The x-ray tubes may be set at similar or varying offsets. These alterations allow the detectors to pick up different x-ray scan data sets for best image quality results. The x-ray tubes may be used simultaneously or in sequence. While not shown, more than two x-ray tubes may be included in the system. In an embodiment, each detector column has an integrated x-ray tube for transmitting x-rays. In an embodiment, an x-ray tube is placed in each gap between detector columns. In an embodiment, an x-ray tube with a non-rotating anode may be used. In an embodiment, an x-ray tube with multiple focal spots may be used for electronically shifting the x-ray source location.

Figure 18:
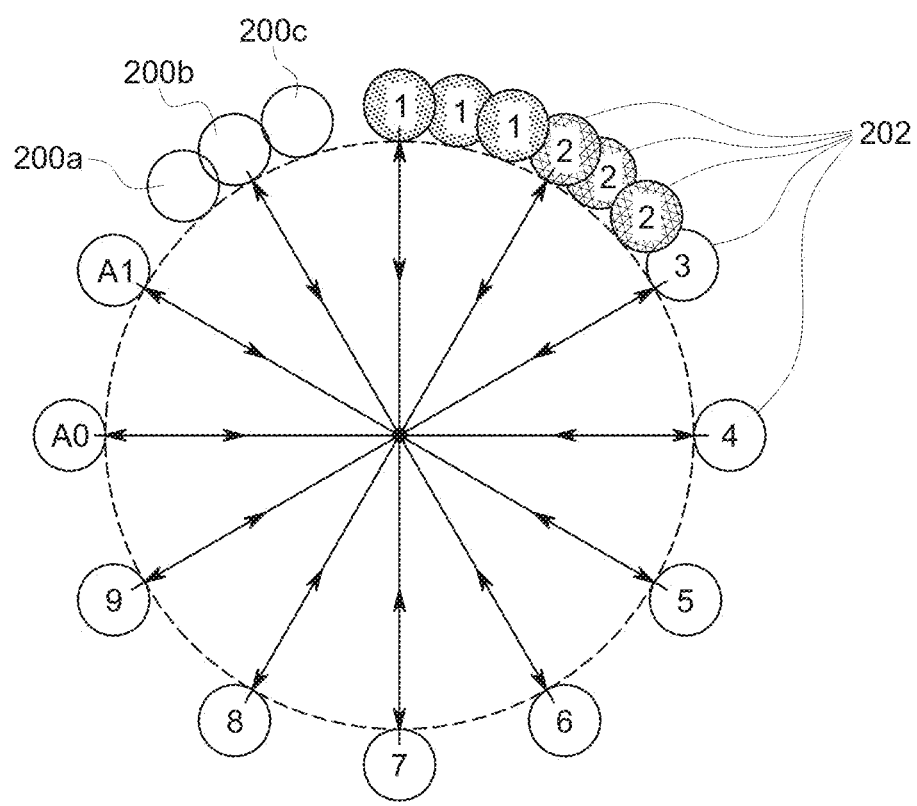
FIG. 18 shows an imaging system where an x-ray tube and image detectors do not rotate, according to an embodiment.

FIG. 18 shows an imaging system where an x-ray tube, in locations 200a, 200b, 200c, and image detectors 202 do not rotate, according to an embodiment. Thus, the system is made simpler and has less chance of rotation maintenance issues. Instead, the x-ray tube and image detectors 202 have multiple steps. Thus, each item in the system has three, for example, step locations. A left, right, and middle, for example. The system has many configurations for scanning and detecting data without having a rotary member. By adjusting the x-ray tube to positions 200a, 200b, and 200c, the system increases the x-ray scan coverage. This multiple step feature can be included in any of the previous embodiments to increase scan data coverage. FIG. 18 also shows an imaging system where the x-ray tube may be retracted or extended towards a subject, according to an embodiment. The patient bed or pallet can have steps as well to position the patient at different location in the X-Y plane, e.g. higher, lower, right, or left. This also provides additional coverage for image detection.

In an embodiment, the system can have one rotary member and one step member. For example, the x-ray tube can be attached to the rotary member for full orbit around a patient. The detector columns can be attached to the step member that only steps into one to three new positions.

Figure 19:
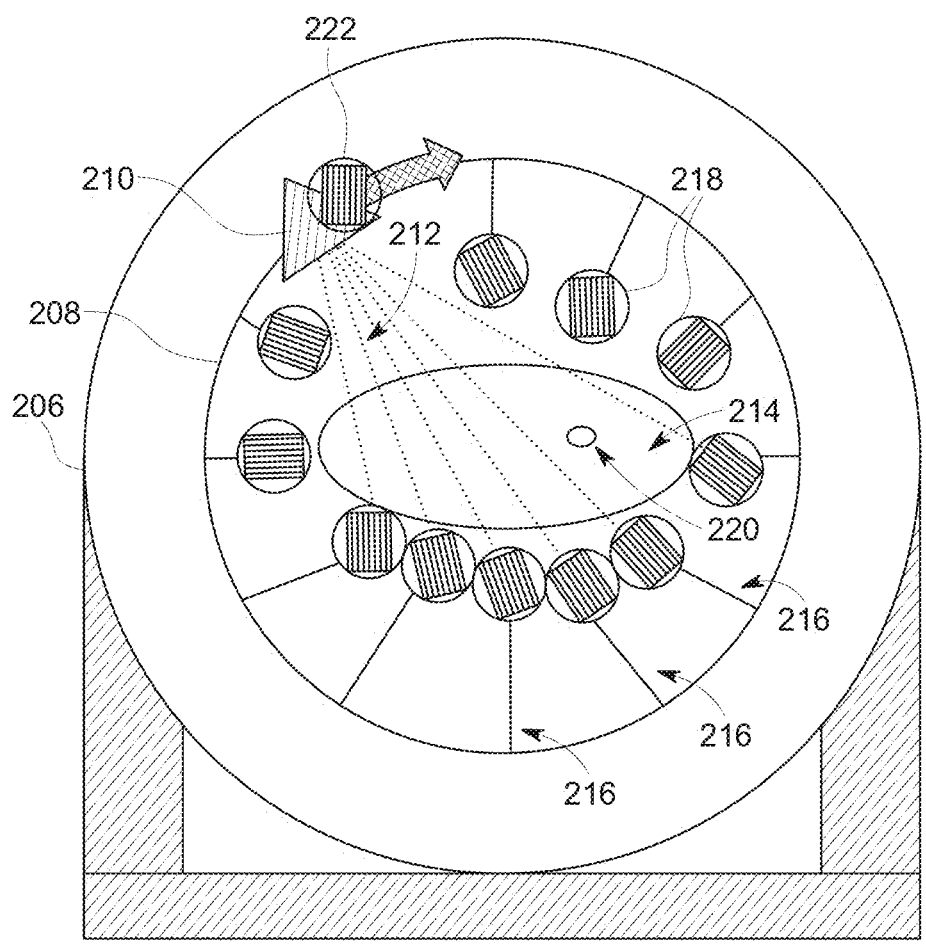
FIG. 19 shows a medical imaging system performing a concurrent NM and CT scan, according to an embodiment.

FIG. 19 shows a medical imaging system performing a concurrent NM and CT scan, according to an embodiment. X-ray tube 210 is attached to rotary member 208. X-ray tube 210 emits x-rays 212 through patient 214 towards dual x-ray/emission active detectors 216. Active image detectors 216, inactive emission detectors 218, and blocked detector 218 can be attached to rotary member 208 or stationary structure 206. Active image detectors 216 have been radially moved towards patient 214 and have their detector heads pointing towards x-ray tube 210. Inactive image detectors 218 have been radially moved towards patient and have their detector heads pointing towards patient ROI 220. Inactive image detectors 218 may also point not just directly to ROI 220, but to define an angular scanning range for small sweeps across the entire ROI 220 distance or width. Blocked detector 218 is retracted to allow pass-by of x-ray tube 210 and may be set into use after x-ray tube 210 has passed.

The system benefits from only needing one orbit of detectors for both CT transmissions and NM/PET emissions. This saves cost and room space from needing to have two sets of detectors. Improvements to the NM/PET image due to attenuation, body shape, ROI determination and other uses of CT data help the system be efficient and provide the best image quality output for users, which may be doctors in an embodiment.

As discussed herein, for example due to gaps between detectors, in some embodiments radiation from an x-ray source may pass through portions of the body without being detected by a detector, resulting in radiation received by a patient that is not used for imaging purposes. By reducing at least a portion of the radiation received by a patient that is not received or detected by a detector, the radiation dose received by the patient may be reduced without comprising image quality. Various embodiments reduce the radiation received by a patient that is not received or detected by a detector using a source collimator (e.g., an adjustable source collimator and/or a collimator having multiple blocking portions separating openings) to reduce the radiation dosage received by a patient. An example embodiment is depicted in FIG. 20.

Figure 20:
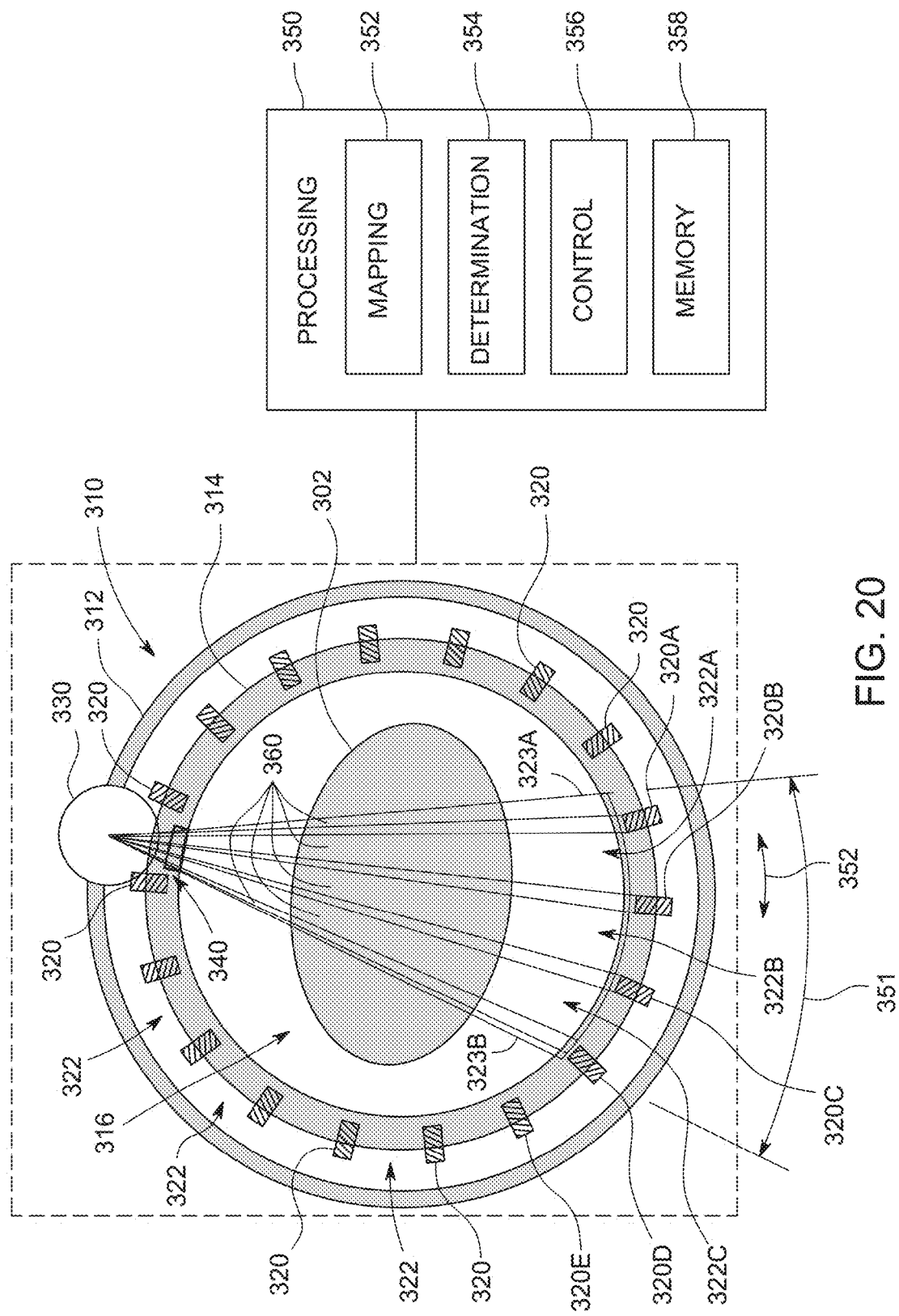
FIG. 20 shows a schematic view of an imaging system, according to an embodiment.

FIG. 20 provides a schematic view of an imaging system 300 in accordance with various embodiments. As seen in FIG. 20, the imaging system 300 includes a gantry 310, a plurality of imaging detectors 320, an x-ray source 330, an adjustable source collimator 340, and a processing unit 350. Generally, the gantry 310 provides a structure for supporting the detectors 320 and the x-ray source 330, as well as for maintaining the detectors 320 and/or x-ray source 330 in a given position, and/or moving the detectors 320 and/or the x-ray source 330 along a given path or trajectory (e.g., a rotation or orbit about a center of a bore of the gantry 310). The imaging detectors 320 are configured to acquire imaging data using x-rays from the x-ray source 330 that have been attenuated by an object to be imaged and/or energy emitted from an object to be image in conjunction with nuclear imaging. The x-ray source 330 emits x-rays over a fan angle 351, with the adjustable source collimator 340 interposed between the x-ray source 330 and the object to be imaged, and is configured to block a portion of the x-rays emitted from the x-ray source 330 to reduce radiation dosage received by a patient being scanned. The processing unit 350 controls one or more aspects of an image acquisition process, including the movement of the x-ray source 330 and/or the detectors 320, or the configuration of the adjustable source collimator 340 to direct x-rays toward the detectors 320 while blocking at least a portion of x-rays that would not impinge upon the detectors 320, among others.

The depicted gantry 310 has a bore 316 extending through the gantry 310. In the illustrated embodiment, the bore 316 is generally circularly shaped and is configured to accept an object 302 (e.g., a patient) to be scanned or imaged. The gantry 310 provides support for the detectors 320 and the x-ray source 330. In the illustrated embodiment, the gantry 310 includes a rotating ring structure 312 and a stationary ring structure 314. The x-ray source 330 is mounted to the rotating ring structure 312, and the rotating ring structure 312 is configured to rotate about the bore 316 of the gantry 310, so that the x-ray source 330 may be rotated about the object 302 disposed in the bore 316 during CT information acquisition. In the illustrated embodiment, the detectors 320 are mounted to the depicted stationary ring structure 314.

It may be noted that, in the illustrated embodiment, the detectors 320 are shown as being in fixed positions uniformly or evenly distributed about the stationary ring structure 312, but that other mountings and/or positionings may be employed in various embodiments. In some embodiments, the detectors 320 may be movable with respect to the stationary ring structure 314. For example, the detectors may be configured to one or more of move radially (e.g., toward or away from center of the bore 316), pivot and/or translate in an imaging plane (e.g., move about a circumference of the bore 316, pivot about an axis parallel to the axis of the bore 316, move upward, downward, or laterally along the plane of FIG. 20), or move axially or in a z-direction (e.g., along or generally parallel to an axis of the bore 316). Additionally or alternatively, in some embodiments, a rotating ring structure may be used instead of a stationary ring structure for mounting the detectors 320. For example, in some embodiments, the detectors 320 may be mounted to a rotating structure and the x-ray source 330 may be mounted to a stationary structure. As another example, the x-ray source 330 may be mounted to a first rotating structure, and the detectors 320 may be mounted to a second rotating structure. The first and second rotating structures may rotate in opposite directions about the bore 316, for example to reduce the amount of time for acquiring 360 degrees worth of CT information without increasing the rotational speed of the x-ray source 330. In some embodiments, the first and second rotating structures may rotate in the same direction, at a different speed, to provide additional adjustability. The x-ray source 330 may be understood as rotating relative to the detectors 320 when the detectors 320 rotate about the bore 316 and the x-ray source 330 is stationary, or rotates in a different direction or at a different speed than the detectors.

As seen in FIG. 20, the depicted imaging detectors 320 are attached to the gantry 316 (e.g., the stationary ring structure 314 in the illustrated embodiment), and are radially spaced around a circumference of the bore 316 such that gaps 322 exist between adjacent image detectors (e.g., detectors 320a, 320b, 320c, 320d) along the circumference of the bore 316. Generally the detectors 320 are oriented toward the object 302 and/or the x-ray source 330 to receive x-rays passing through the object 302 and/or emission radiation from the object 302. The detectors 320 may pivot (or the sweep angle of the detectors may vary) during rotation to maintain orientation of detector surfaces toward the x-ray source 330. The detectors 320 may be generally similar in certain respects to detectors discussed in connection with other embodiments herein.

In the illustrated embodiment, detector 320a is adjacent to detector 320b, with gap 322a interposed between detector 320a and 320b. As seen in FIG. 20, detector 320a is adjacent to detector 320b, with gap 322a interposed between detector 320a and 320b. Also, detector 320b is adjacent to detector 320c, with gap 322b interposed between detector 320b and 320c. Also, detector 320c is adjacent to detector 320d, with gap 322c interposed between detector 320c and 320d. Further, gap 323a is located between the edge of the detector 320a and an edge (the right-most edge or counter-clockwise most edge as seen in FIG. 20) of the full beam spread 354 defined by the fan angle 351, and gap 323b is located between the edge of the detector 320d and an edge (the left-most edge or clockwise most edge as seen in FIG. 20) of the full beam spread 354. X-rays that pass through the gaps 322a, 322b, 322c, 323a, and 323b are not received by any of the detectors 320 and thus are not used in imaging, resulting in unused radiation being received by the object 302. By eliminating or reducing the X-rays passing through such gaps with a source collimator or pre-patient collimator, various embodiments reduce the radiation dosage received by the object 302 without reducing the amount of imaging information collected. In various embodiments, at least one of the imaging detectors 320 is configured to detect both emission radiation and x-ray radiation.

The depicted x-ray source 330 is attached to the gantry 310 (e.g., mounted to the rotating ring structure 312 in the illustrated embodiment) and transmits x-rays across the bore 316, through the object 302, and toward at least two of the image detectors 320. The x-ray source 330, for example, may be configured as an x-ray tube having an opening through which x-rays generated by the tube are allowed to pass, with the opening oriented toward the center of the bore 316 or toward the object 302 being imaged. In the illustrated embodiment, four detectors (320a, 320b, 320c, 320d) are within the full beam spread 354 defined by the fan angle 351. As the x-ray source 330 is rotated about the circumference of the bore 316, the particular detectors 320 receiving x-rays and the position of the detectors 320 receiving x-rays relative to the x-ray source 330 will change. For example, when the x-ray source 330 is rotated to a position slightly clockwise of the position shown in FIG. 20, only a portion of the detector 320a will receive x-rays. When the x-ray source 330 is rotated still further clockwise, none of the detector 320a will receive x-rays. As the x-ray source 330 continues to rotate clockwise, detector 320e (adjacent to detector 320d) will begin to receive x-ray radiation. As the x-ray source 330 makes a complete rotation about the bore 316, each of the detectors 320 will move into and/or out of a field of view or full beam spread 354 defined by the fan angle 351. Generally, the x-ray source 330 rotates about the object 302 relative to the detectors to provide CT information that may be used to generate a three dimensional image. The x-ray source 330 may perform a complete rotation or 360 degrees with respect to the detectors 320 in some embodiments during CT information acquisition, or may be rotated more or less in various embodiments. As indicated herein, in some embodiments the x-ray source 330 may rotate relative to the detectors 320 via maintaining the x-ray source 330 in a stationary position while the detectors 320 rotate about the bore 316, or as another example, via a rotation of the x-ray source 330 in an opposite direction to a rotation of the detectors 320. The x-ray source 330 may be generally similar in certain respects to x-ray sources discussed in connection with other embodiments herein.

The depicted adjustable source collimator 340 is interposed between the x-ray source 330 and a center of the bore 316, such that x-rays from the x-ray source 330 must pass through the adjustable source collimator 340 before passing through the object 302. The adjustable source collimator 340 is configured to block a portion of the x-rays produced by the x-ray source 330 along the fan angle 351 in the scanning direction 352 defined by the circumference of the bore 316. For example, in various embodiments, the adjustable source collimator 340 includes at least one opening interposed between blocking portions, with the opening configured to allow passage of x-rays through the adjustable source collimator 340, and the blocking portions made of a material configured to impede or prevent passage of x-rays. By varying the amount and location of x-rays that are allowed to pass through the adjustable source collimator 340, the amount and location of x-rays allowed to impinge upon the object 302 may be controlled, for example to reduce dosage by blocking x-rays that are not directed to be received by one of the detectors 320. The adjustable source collimator 340 may also be referred to as a pre-patient collimator. A source or pre-patient collimator is interposed between the x-ray source and an object to be imaged, in contrast to detector collimators which are interposed between a detector and an object to be imaged and configured to direct radiation to a specific portion (e.g., one or more pixels) of a detector.

Generally, the adjustable source collimator 340 is controlled to limit transmission of at least a portion of the x-rays in the full beam spread 354. For example, the adjustable source collimator may have blocking portions and/or openings that are adjustable at least partially along direction 352 along the fan angle 351 to limit transmission of one or more portions of the full beam spread 354. In some embodiments, the adjustable source collimator 340 may be controlled to allow passage of x-rays corresponding to detectors for which the complete detector is receiving x-rays from the x-ray source 330, but to block at least a portion of other portions of the full beam spread 354. In various embodiments, different techniques may be employed for adjusting the adjustable source collimator, or adjusting the locations of x-rays or portions of x-rays produced by the x-ray source 330 permitted to pass on to the object 302 being imaged. For example, in some embodiments, the size of an opening may be varied (e.g., by moving one or more blocking portions defining a size of the opening). As another example, an adjustable source collimator may include one or more openings having a fixed size, with the adjustable source collimator 340 controlled by varying a position of one or more fixed openings (e.g., by laterally translating the fixed opening relative to the x-ray source). Additionally or alternatively, in various embodiments, one or more openings may also be variable in a z-direction (with a z-direction defined as a direction along the axis of the bore 316) for additional control or adjustability.

For example, for the embodiment depicted in FIG. 20, a maximum of four detectors may be in the fan angle 351 or field of view at one time. The depicted adjustable source collimator 340 may be provided with four openings to allow for up to four separate ranges or portions of x-rays to be permitted to pass through the adjustable source collimator 340 and object 302 to the detectors 320 within the fan angle 351 or field of view at a given time during rotation of the x-ray source 330 relative to the detectors. At the position shown in FIG. 20, four detectors (320a, 320b, 320c, 320d) are within the fan angle 351. Accordingly, all four openings of the adjustable source collimator 340 may be in an open state to permit passage of x-rays to the detectors 320; 320b, 320c, 320d, while blocking portions interposed between the openings act to reduce the amount of x-rays allowed to pass to the object 302 that will not impact one of the detectors 320 after passage through the object 302.

As the x-ray source 330 rotates clockwise, the detector 320a will cease to remain within the fan angle 351 or field of view. Accordingly, as the detector 320a goes out of the field of view, the adjustable source collimator 340 may be controlled to close off the opening corresponding to the furthest counter-clockwise position (e.g., the position corresponding to detector 320a), so that, with only three detectors (320b, 320c, 320d) within the field of view or fan angle 351, only 3 openings are open to permit passage of x-rays. Further, the size of the openings or position of the openings that remain open may be shifted or adjusted to help direct the x-rays to the changing positions of the detectors within the field of view relative to the x-ray source 330 as the x-ray source 330 rotates.

As the x-ray source 330 rotates further clockwise, the fan angle 351 or field of view will encounter and include detector 320e in addition to detectors 320b, 320c, 320d. Accordingly, the adjustable source collimator 340 may be controlled to again place the previously closed opening in an open condition to permit four discrete angular ranges of x-rays to pass through the adjustable source collimator 340. Further, the openings may be shifted to change the particular detector to which a given opening directs x-rays. For example, an opening previously directing x-rays to detector 320d may be shifted to direct x-rays to detector 320e, an opening previously used for detector 320c may be shifted to detector 320d, an opening previously used for detector 320b may be shifted to detector 320c, and the newly opened opening (e.g., the opening previously used for detector 320a before detector 320a left the field of view) may be used for detector 320b. It may be noted that the above example is provided for illustrative purposes only. For example, the timing of shifting of x-rays from one opening from one detector to another may occur at a different time. It may also be noted that the adjustments to the openings of the adjustable source collimator 340 may be performed relatively quickly in various embodiments, as the x-ray source 330 may perform a complete rotation in less than a second, for example in about 0.25 seconds or less.

Figure 21:
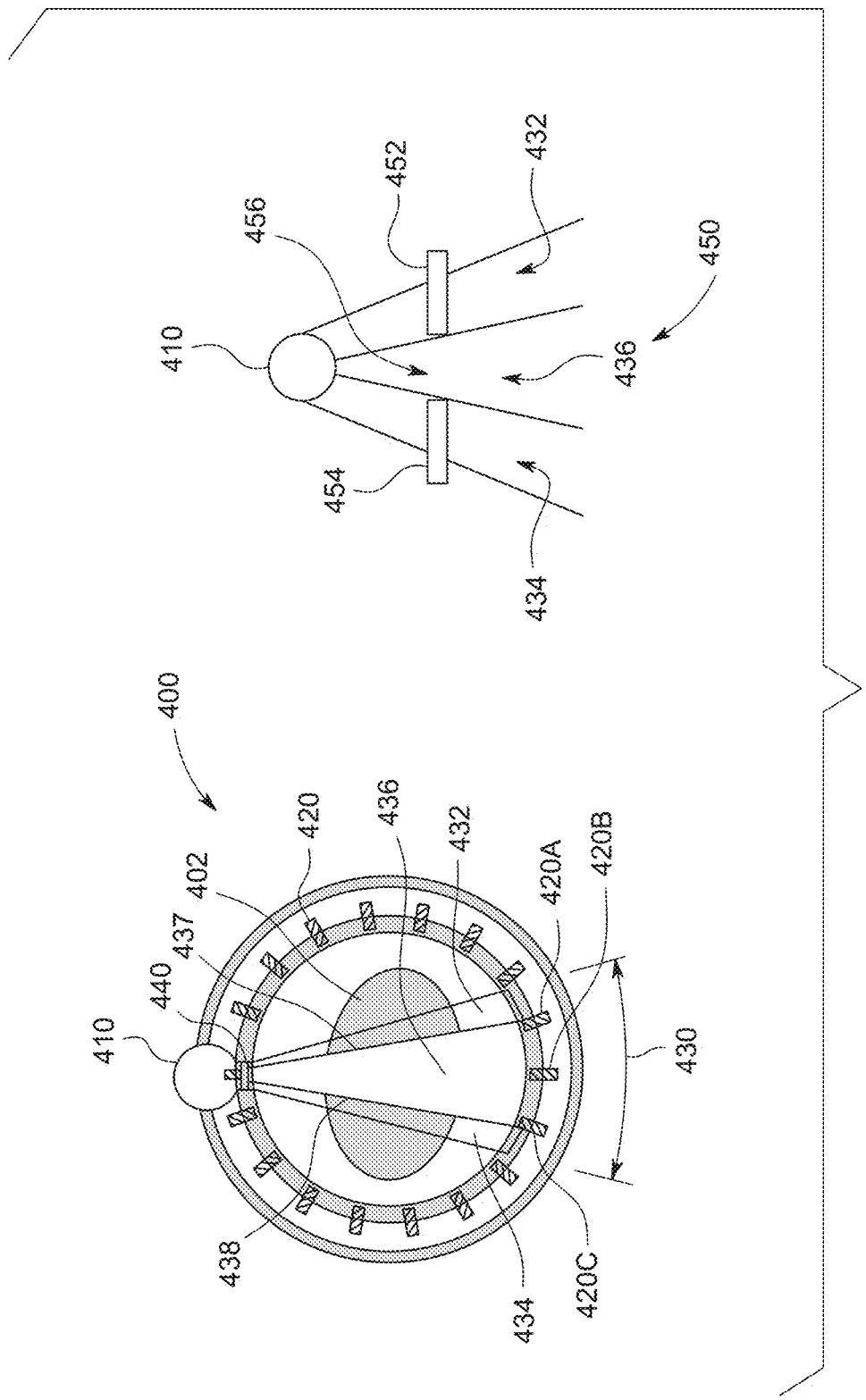
FIG. 21 shows a schematic view of an imaging system, according to an embodiment.

In some embodiments, the processing unit 350 may be configured to dynamically adjust outer boundaries of the fan angle 351 to correspond to a range defined by the detectors 320 within the fan angle 351 at a given point during the rotation of the x-ray source 330. For example, the adjustable source collimator 340 may have a single opening with an adjustable width that is controlled based on the position of the detectors 320 within the fan angle 351 to allow passage of x-rays to all detectors 320 within the fan angle 351 while blocking x-rays on either side of the outermost detectors 320 within the fan angle 351. FIG. 21 provides a schematic view of an imaging system 400 in accordance with various embodiments. Generally, the various components of the imaging system 400 may be generally similar in respects to the imaging system 300. The imaging system 400 includes an x-ray source 410, detectors 420, and an adjustable source collimator 440. The x-ray source 410 directs x-rays over a fan angle 430 toward the detectors 420 through an object 402 to be imaged, with the adjustable source collimator 440 limiting the passage of at least a portion of the x-rays from the x-ray source 410 through the object 402.

As seen in FIG. 21, three detectors (420a, 420b, 420c) are within the fan angle 430. The adjustable source collimator 440, at the illustrated position, is controlled to have an opening sized and position to allow an interior range 436 of x-rays from the fan angle 430 to pass through to the detectors 420a, 420b, 420c, while blocking exterior portion 432 and exterior portion 434 (which do not impact any detectors) from passage to the object 402. The fan angle 351 thus includes an outer boundary 437 (between range 436 and range 432) and an outer boundary 438 (between range 436 and range 434) that define the amount and location of x-rays allowed to pass through to the object 302. The adjustable source collimator 340 may be controlled to adjust the outer boundary 437 and the outer boundary 438 to provide a range of x-rays that pass through the object 402 corresponding to the detectors 420. It may be noted that the outer boundaries 437, 438 may not coincide exactly with the edges of the outermost detectors within the field of view. Instead, the boundaries may be located slightly outwardly of the detectors to help insure full coverage of each detector within the field of view and to reduce any image quality issues associated with the impact of an edge of a beam on a detector.

Generally, the adjustable source collimator 440 may include a single opening that has an adjustable width that is controlled to adjust the outer boundaries 437, 438 of the fan angle permitted to pass toward the object 402. The opening may be adjustable in terms of width and/or position relative to the x-ray source 330. For example, as best seen in view 450 of FIG. 21, the adjustable source collimator 440 may include a first blocking plate 452 and a second blocking plate 454 defining an opening 456 therebetween. X-rays passing through the opening 456 provide the range 436 of x-rays that pass on to the object 402, while the first blocking plate 452 blocks x-rays to provide the exterior portion 432 of x-rays that are blocked from passage to the object 402, and the second blocking plate 454 blocks x-rays to provide the exterior portion 434 of x-rays that are blocked from passage to the object 402. By moving the first blocking plate 452 and the second blocking plate 452 at the same time and at symmetric distances relative to the center of the opening 456, the range 436 may remain centered relative to the x-ray source 410 while increasing or decreasing the size of the opening 456. To shift the position of the opening 436 relative to the x-ray source, the blocking plates may be moved in a non-symmetric fashion with respect to the center of the opening 436. For example, to maintain the size of the opening 436 but shift the opening to the right as seen in FIG. 4, the first blocking plate 452 and the second blocking plate 454 may be moved the same distance as each other to the right. The imaging system 400 accordingly allows for blockage of x-rays corresponding to exterior gaps (e.g., gaps 323a, 323b of FIG. 20), while using a relatively simple collimator employing a single adjustable opening. Thus, the blocking plates may be adjusted so that the opening allows passage of x-rays to detectors but blocks external portions of the fan angle that are not directed toward detectors during rotation of the x-ray source 410 about the object 402. It may be noted that, while the imaging system 400 provides some reduction in dosage and has a relatively straightforward mechanical design and relatively straightforward control scheme, that the adjustable source collimator 440 does not block x-rays through the object 402 through internal gaps between the detectors (e.g., a gap between detector 420a and detector 420b, the gap between detector 420b and detector 420c).

Figure 22:
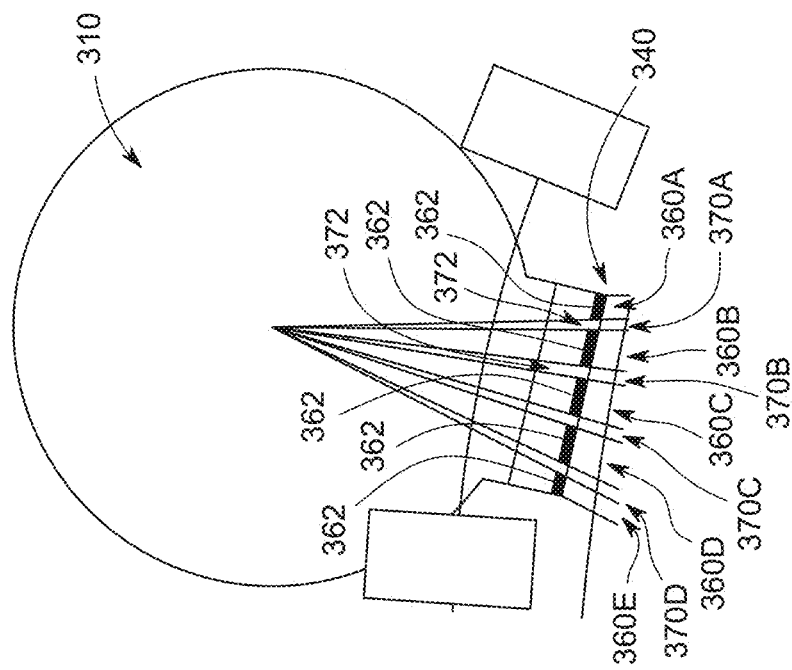
FIG. 22 shows an enlarged view of aspects of the imaging system depicted in FIG. 20.

In order to block interior gaps between detectors as well as exterior gaps between detectors and the edge of the fan beam, in various embodiments an adjustable source collimator may be provided that includes a plurality of openings separated by blocking portions along the fan angle. The adjustable source collimator 340 discussed in conjunction with FIG. 20 provides an example of an adjustable source collimator having a plurality of openings. FIG. 22 provides an enlarged view of the adjustable source collimator 340 depicted in FIG. 20. As seen in FIG. 22, the adjustable source collimator 340 includes a plurality of openings 372 separated by blocking portions 362. X-rays passing through the openings 372 provide ranges 370 of x-rays that are allowed to pass through to an object being imaged. As seen in FIG. 22, the range of x-rays allowed to pass through includes a number of sub-ranges, namely ranges 370a, 370b, 370c, 370d. It may be noted that the size and/or positioning of the openings may be controlled so that the ranges allowed to pass through the object correspond to the detectors within the field of view at a given point during the rotation of the x-ray source 310 about the object to be imaged. The ranges allowed to pass through may correspond to ranges that will impact a detector surface (or detected portions) determined based on detector positions relative to the x-ray source. The ranges allowed to pass through the adjustable source collimator 340 may be slightly larger than the theoretic ranges that coincide with detector edges to help insure complete coverage of the detectors and to reduce or eliminate image quality issues associated with the edge of a beam impacting a detecting surface.

As also seen in FIG. 22, the range of x-rays blocked by the blocking portions 362 or not permitted to pass to the object being imaged includes a number of sub-ranges, namely ranges 360a, 360b, 360c, 360d, and 360e. The blocking portions 362 may be controlled to vary the position and/or the size of the openings 372 during rotation of the x-ray source 310 relative to the detectors to advantageously allow passage of x-rays directed toward detectors while inhibiting passage of x-rays not directed toward detectors at the various positions of the x-ray source about the circumference of the bore of the gantry during acquisition of CT information. The ranges not allowed to pass through or impeded from passage may correspond to ranges that will not impact a detector surface (or non-detected portions) determined based on detector positions relative to the x-ray source. Systems employing adjustable source collimators having multiple openings as seen in FIG. 22 are more mechanically complex and have more complex control schemes than systems having a single opening as seen in FIG. 21, but provide for additional reduction in radiation dosage seen by an object (e.g., human patient) being imaged.

Various mechanical arrangements and corresponding control schemes may be used to provide adjustable collimators having multiple openings. Generally, the size and/or position of the openings are controlled as a function of rotational position of the x-ray source based on the position and orientation (e.g., angle of pivot toward x-ray source 330) of the detectors within the field of view of the x-ray source at each rotational position. For example, for uniformly spaced detectors fixed in position with an x-ray source rotating at a constant angular speed, the width of the openings as well as the positioning of the centerlines of the openings may vary as a function of rotational position in a repeating pattern as the x-ray source rotates. The pattern may be the same for each opening, with a phase lag between the openings. However, if the radial position of the detectors (e.g., distance from center of the bore of a gantry) differ from each other, if the detectors are not uniformly spaced, if the orientations of the detectors vary, and/or if the detectors are moved during rotation of the x-ray source, the control scheme of the openings may become more complex.

It may further be noted that, in various embodiments, the system may also detect or otherwise determine which locations (e.g., locations about the bore of a gantry) do not have detectors, for example in a partially populated system. For example, in some embodiments, a plurality of detector locations configured for mounting detectors may be distributed about a gantry. However, for some scans, not all of the detector locations may be used, and some of the detector locations may not have a detector installed for a particular application or type of scan. The system may detect or determine which detector locations do not have an installed detector, and control the adjustable source collimator to prevent or inhibit the passage of x-rays that are directed toward detector locations for which no detector is installed (or otherwise active). Additionally or alternatively, the system may also detect or otherwise determine which of the present detectors are inoperable for a given scan, and/or which of the present detectors may be unnecessary, undesired, or inappropriate for use in conjunction with a given scan. A detector may be understood as inoperable, for example, when the detector is broken, malfunctioning, does not have CT detection capability, and/or is unable to sweep its detector head to point towards the x-ray source during an imaging operation. In various embodiments, the system dynamically updates the source collimator to block x-ray radiation from reaching those locations with no detector or an inoperable detector.

In some embodiments, the openings of an adjustable source collimator may have a fixed width. FIGS. 23A-C provide schematic views of an adjustable source collimator 500 having fixed width openings 510 separated by blocking portions 511 interposed therebetween. In the illustrated embodiment, the adjustable source collimator 500 is configured to collimate x-rays emitted from a focal point 502 (e.g., a focal point inside an x-ray tube). The adjustable source collimator 500 includes a movable plate 520 and a fixed plate 528. The fixed plate 528 is fixed relative to the focal point 502, while the movable plate 520 is configured to be translated laterally across a face of the fixed plate 528. The movable plate 520 includes a plurality of fixed width openings 510 (five total in the illustrated embodiment), and the fixed plate includes an opening 512. The opening 512 is large enough to include all of the fixed width openings 510 within an envelope or footprint of the opening 512 when the movable plate 520 is centered relative to the fixed plate 528 (see, e.g., view 530). The movable plate 520 may be coupled to an articulation member (not shown) configured to laterally translate the movable plate 520 responsive to control signal received from a processing unit (e.g., processing unit 350).

In FIG. 23B, the movable plate 520 is shown centered with respect to the fixed plate 528. In such a position, all five fixed width openings 510 are in view of the focal point 502, and thus five discrete angular ranges of x-rays passed from the fan angle from the focal point 502 will impact the object being imaged. Such an arrangement may be employed when five detectors are within the field of view. As the x-ray source rotates relative to the detectors, the movable plate 520 may be articulated to shift the direction of the passed ranges of x-rays to correspond with the shifting position of the detectors relative to the x-ray source. For example, the movable plate 520 may be shifted to the right in the sense of FIG. 23, resulting in the fixed width openings 510 (and corresponding ranges of x-rays allowed to pass on toward the object being imaged) moving to the right relative to opening 512 and the focal point 502.

As the movable plate 520 is continued to be translated to the right, the movable plate 520 will reach the position shown in FIG. 23C. As seen in FIG. 23C, the movable plate 520 has moved sufficiently to the right such that the opening 510a is no longer within the footprint or envelope of the opening 512, and such that the solid portion of the fixed plate 528 blocks x-rays from the focal point 502 directed toward the opening 510a. In such a position, only four of the five fixed width openings 510 are in view of the focal point 502, and thus four discrete angular ranges of x-rays passed from the fan angle from the focal point 502 will impact the object being imaged. Such an arrangement may be employed when four detectors are within the field of view. Thus, the movable plate 520 may be articulated to control the number of ranges of x-rays allowed to pass through (based on the number of detectors within the field of view) as well as control the direction of the ranges of x-rays allowed to pass through (based on the positions of the detectors within the field of view relative to the x-ray source). The position of the movable plate 520 may be controlled as a function of x-ray source position as the x-ray source rotates about an object to be imaged relative to the detectors.

Figure 24:
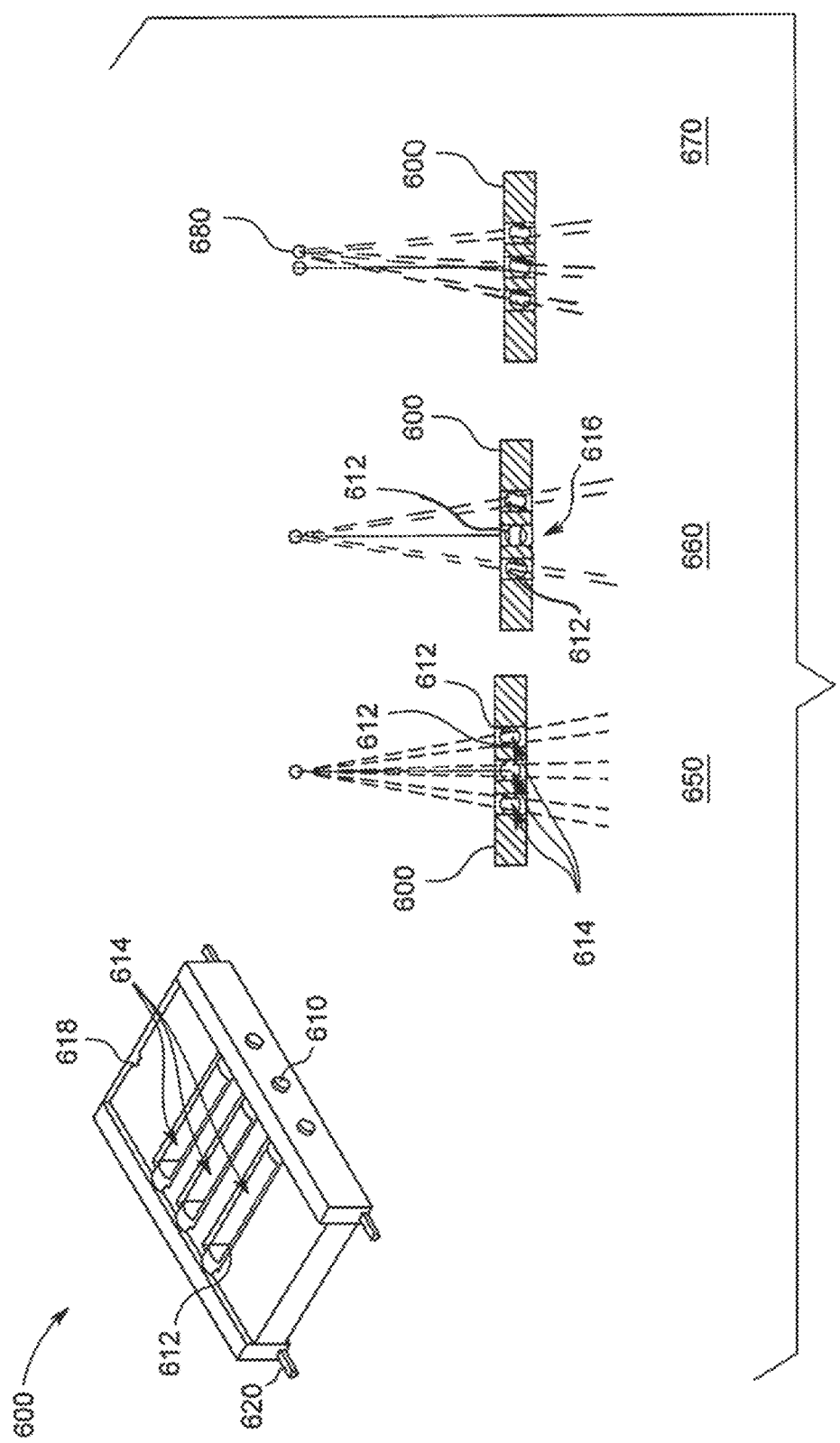
FIG. 24 shows a schematic view of an adjustable collimator, according to an embodiment.

As another example, in some embodiments, at least one of the openings of an adjustable source collimator having plural openings may have an adjustable width. As discussed in connection with FIG. 21 herein, an opening may be adjusted by laterally articulating one or more blocking plates. As another example, one or more rotary members may be employed to adjust the width of one or more corresponding openings of an adjustable source collimator. FIG. 24 provides a schematic illustration of an adjustable collimator 600 that utilizes rotary members to vary an adjustable width of openings of the adjustable source collimator 600 in accordance with various embodiments.

As seen in FIG. 24, the adjustable source collimator 600 includes a frame 618 having rotors 610 extending through central openings of the frame 618. The rotors 610 include openings 614 extending therethrough and blocking portions 612 defining boundaries of the openings 614. The rotors 610 provide an example of rotary members used to adjust widths of openings permitting passage of x-rays through an adjustable source collimator. To vary the effective width of the openings of the adjustable source collimator 600, the rotors 610 may be rotated by a rotating mechanism (not shown) such as a motor coupled to one or more rotors. The rotors 610 may be rotated independently of each other in some embodiments to provide independently adjustable collimator opening widths. The frame 618 also includes rails 620. The frame 618 may be mounted to a ring structure or other support structure via the rails 620 to provide for lateral motion relative to an x-ray source to provide additional adjustability of the adjustable source collimator 600.

When adjusted to the position shown in view 650, the adjustable source collimator 600 permits passage of three generally similarly sized ranges of x-rays to pass through the adjustable source collimator 600 and on to an object to be imaged. To vary the width of one or more openings (and the corresponding widths of one or more ranges of x-rays allowed to pass through the adjustable source collimator 600) and/or to reduce the number of ranges permitted to pass through the adjustable source collimator 600, one or more rotors 610 may be rotated. For example, as seen in view 660, a middle rotor 616 has been rotated so that the blocking portions 612 of the rotor 616 cooperate to block x-rays from passage through the portion of the adjustable source collimator associated with the middle rotor 616. In the position shown in view 660, only two ranges of x-rays will be allowed to pass through the adjustable source collimator 600. The position shown in view 660 may be employed when only two detectors are within a field of view of the x-ray source. Alternatively or additionally, the position in view 660 may be employed when the portion of the object that would be illuminated by x-rays passing through the rotor 616 is not of interest, allowing for further reduction of radiation dosage. For additional adjustment (e.g., changing of position of ranges of x-rays provided to the object relative to the x-rays in addition to changing of widths of ranges), the adjustable source collimator may be moved laterally with respect to the x-ray source. As seen in view 670, the adjustable source collimator 600 has been shifted in position (to the left relative to a centered position of x-ray source 680 in view 670).

The rotors 610 of the adjustable source collimator 600 may be rotated to control a width of x-ray ranges permitted to pass through to an object to be imaged, while the direction or orientation of the permitted ranges may be controlled by lateral movement of the frame 618 relative to the x-ray source. The rotational positions of the rotors and/or the lateral position of the frame 618 provided may be controlled to provide a desired number of ranges of x-rays passed through the adjustable source collimator 600, a desired width of the ranges, and/or a desired direction of ranges based on the number of detectors and the positions of the detectors within the field of view of an x-ray source as a function of position of the x-ray source as the x-ray source rotates about an object to be imaged.

Figure 25:
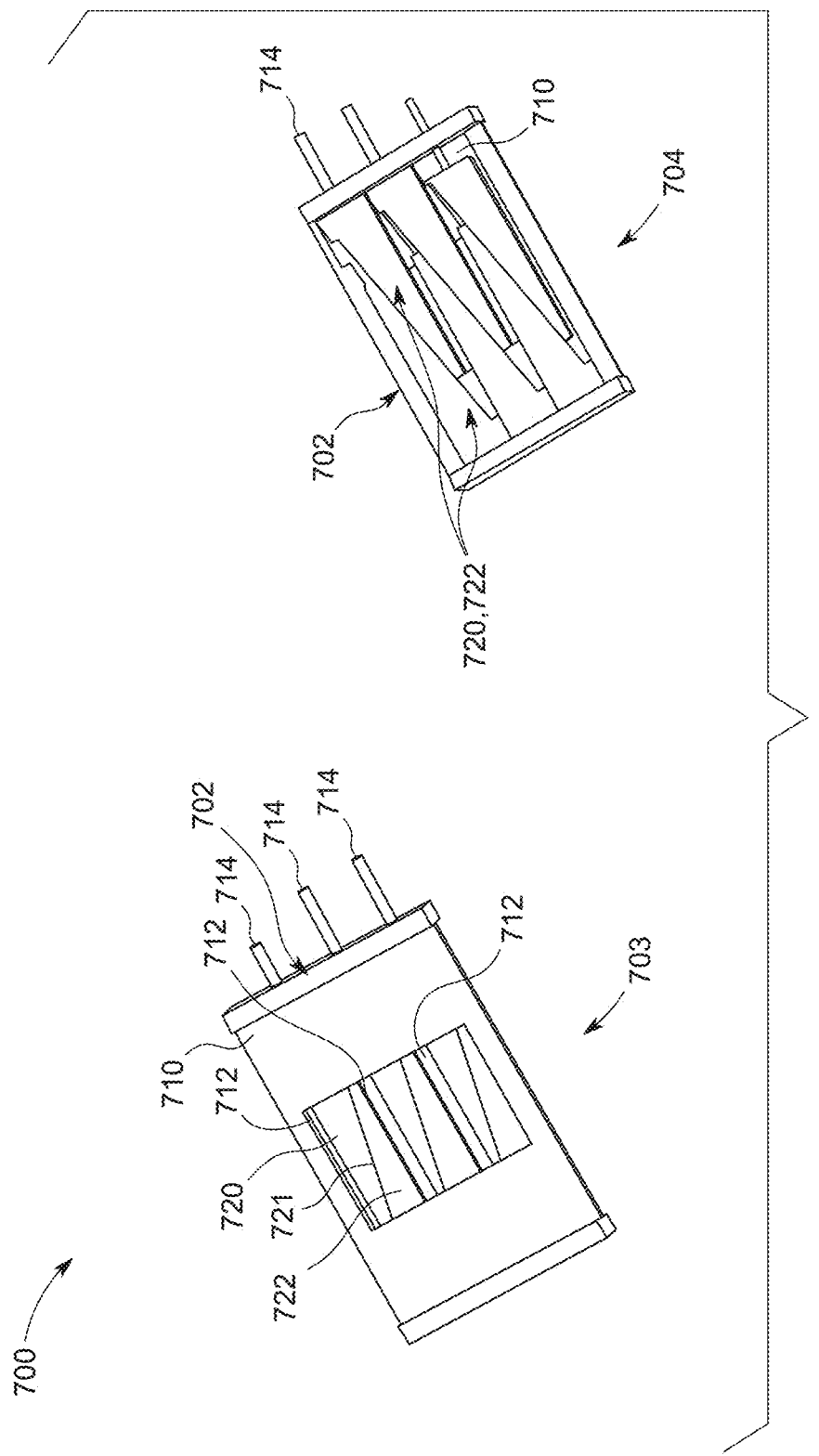
FIG. 25 shows a schematic view of an adjustable collimator, according to an embodiment.

Other techniques or arrangements may be employed to vary an adjustable width of an opening of an adjustable source collimator. As one additional example, FIG. 25 provides a schematic view of an adjustable source collimator 700 in accordance with various embodiments. The adjustable source collimator 700 includes a frame 702, a cover plate 710, articulation members 714, and cooperating aperture plates 720, 722. View 703 provides a view of the adjustable source collimator 700 from an x-ray exit side and view 704 provides a view of the adjustable source collimator 704 from an x-ray inlet side. Generally, a given articulation member 714 is controlled to be moved toward or away from an interior of the frame 702 along a length of the frame 702, thereby urging a corresponding aperture plate 722 to be translated across a length of the frame 702. As the aperture plate 722 moves along the length of the frame 702, the corresponding cooperating aperture plate 720 is urged along the width of the frame 702 by the sloped interaction surface 721 between the aperture plate 722 and the aperture plate 720. The movement of the aperture plate 720 across the width of the frame 702 acts to vary the width of a corresponding opening 712.

Returning to FIG. 20, the depicted processing unit 350 is operably coupled to the adjustable source collimator 340, and is configured to control the adjustable source collimator 340 to dynamically adjust a range of x-rays that are blocked by the adjustable source collimator 340 along the fan angle 351 during transmission of the x-rays from the x-ray source 330 and acquisition of CT information by detectors 320.

The processing unit 350, for example, may receive and/or determine information describing, depicting, or corresponding to the positions of the detectors 320 with respect to the x-ray source 330 as the x-ray source 330 rotates relative to the detectors 320. Using such positioning information, the processing unit 350 may determine which portions of the x-rays emitted from the x-ray source 330 will impact detectors (and which particular detectors will be impacted), and provide an output to control the adjustable source collimator 340 to permit passage of the x-rays that will impact upon detectors while blocking or impeding passage of at least a portion of x-rays that will not impact upon detectors. As another example, the processing unit 350 may provide control signals to one or more aspects of the imaging system 300, such as the x-ray source 330 (e.g., to activate the x-ray source 330), the detectors 320 (e.g., to activate detectors or associated components within a field of view, to switch detectors or associated components within the field of view to an x-ray detection mode, to have the respective detector head sweep to point towards x-ray source 330), and/or the rotating ring structure 312 (e.g., to rotate the x-ray source about an object to be imaged).

In various embodiments the processing unit 350 includes processing circuitry configured to perform one or more tasks, functions, or steps discussed herein. It may be noted that "processing unit" as used herein is not intended to necessarily be limited to a single processor or computer. For example, the processing unit 350 may include multiple processors and/or computers, which may be integrated in a common housing or unit, or which may distributed among various units or housings. It may be noted that operations performed by the processing unit 350 (e.g., operations corresponding to process flows or methods discussed herein, or aspects thereof) may be sufficiently complex that the operations may not be performed by a human being within a reasonable time period. For example, the mapping of detector positions with respect to the x-ray source, determination of the position of the x-ray source, determination of the portions of a fan angle of x-rays that will impact upon detectors, and the determination of control inputs to the adjustable source collimator to block at least a portion of x-rays not impacting detectors may rely on or utilize computations that may not be completed by a person within a reasonable time period. The speeds of rotation and scanning in such a system operate much faster than a human could compute the needed information.

In the illustrated embodiment, the processing unit includes a mapping module 352, a determination module 354, a control module 356, and a memory 358. It may be noted that other types, numbers, or combinations of modules may be employed in alternate embodiments, and/or various aspects of modules described herein may be utilized in connection with different modules additionally or alternatively. Generally, the various aspects of the processing unit 3500 act individually or cooperatively with other aspects to perform one or more aspects of the methods, steps, or processes discussed herein.

The depicted mapping module 352 is configured to determine the location of detectors within a field of view of the x-ray source 330 as the x-ray source 330 rotates about the bore 316 of the gantry. Based on the positions (e.g., location about circumference of bore, radial distance from center of bore, orientation of detector surface relative to x-ray source) of the detectors, the portions of the fan angle that will impact detectors and the portions of the fan angle that will not impact detectors may be determined. In some embodiments, the position of the detectors may be based on a priori knowledge of known or specified pre-determined positions of the detectors during CT acquisition. For example, if the position of the detectors is fixed, the determination of the corresponding configurations and variation of the adjustable source collimator may be relatively straightforward geometrically. However, the determination of position (and corresponding adjustable source collimator configuration) may become more complex when the detectors are not fixed or uniformly spaced, when some detectors may be inoperable, uninstalled, or otherwise inactive and/or when one or more detectors moves during CT information acquisition.

Accordingly, in some embodiments, the position of the detectors 320 relative to the x-ray source 330 as the x-ray source 330 rotates may be determined additionally or alternatively using a test rotation of the x-ray source 330. For example, before the object is placed within the bore, but with the detectors controlled to be positioned as they would be for the actual scan, the x-ray source 330 may be activated to emit x-rays and rotate about the bore 316. As the x-ray source rotates about the bore, the positions of the detectors, and which detectors are receiving radiation from the x-ray source may be determined as a function of x-ray source rotational position using information acquired by the detectors (e.g., information describing which detectors or portions thereof are receiving x-rays at various rotational positions of the x-ray source). The position of the x-ray source 330 may be determined using an associated positional sensor. It may be noted that the determination of detector locations (and ranges of x-rays that will impact or not impact the detectors) as a function of x-ray source position may be determined using both a priori knowledge of detector positions and a test run. For example, an initial estimate of detector position as a function of rotational position of the x-ray source may be generated using known or estimated detector positions, with a test run used to confirm (and modify as appropriate) the initial estimation.

In the illustrated embodiment, the depicted determination module 354 is configured to determine settings of the adjustable collimator as a function of rotational position of the x-ray source to permit passage of x-rays corresponding to detector positions within the field of view and to block at least a portion of x-rays that will not impact detectors, based on a mapping of the detectors relative to the x-ray source provided by the mapping module 352. Based on the ranges of x-rays emitted by the x-ray source that will be received by detectors and portions that will not be received by detectors, the determination module 354 determines settings of the adjustable source collimator 340 (e.g., position of blocking portions to provide a desired width and/or position of opening) to provide the desired passage of x-rays to detectors. As noted herein, the settings of the adjustable source collimator 340 may be selected to permit passage of some x-rays that will not impact detectors to provide a safety margin (e.g., to insure full coverage of all detector surfaces within the field of view) and to avoid any image quality issues that may result from an edge of an x-ray beam impacting on or near a detector.

The depicted control module 356 is configured to provide control signals (e.g., to translate a movable plate having fixed openings, to translate a blocking plate, to rotate a rotor, or the like) to the adjustable source collimator as the x-ray source 330 rotates relative to the detectors 320 to implement the settings determined by the determination module 340. The control signals may be used to vary a width of one or more openings (e.g., based on a change in position of a detector relative to the x-ray source), to change a position of one or more openings (e.g., based on a change in position of a detector relative to the x-ray source), and/or to open or close one or more openings (e.g., based on a change in total number of detectors within a field of view).

The memory 358 may include one or more computer readable storage media. The memory 358, for example, may store mapping information describing the position of detectors, acquired CT information, image data corresponding to images generated, results of intermediate processing steps, or the like. Further, the process flows and/or flowcharts discussed herein (or aspects thereof) may represent one or more sets of instructions that are stored in the memory 358 for direction operations of the system 300.

Generally, in various embodiments, the processing unit 350 is configured to determine the presence of CT operable detectors within a field of view and the positions of such detectors within the field of view as a function of the rotational position of the x-ray source relative to the detectors, and to determine and implement settings for the adjustable source collimator to provide x-rays to the detectors within the field of view while impeding passage of x-rays that will not impact the detectors. It may be noted that the positions of the detectors may be determined at various discrete positions about a circumference of the bore, with the position of the detectors and corresponding settings for the adjustable source collimator interpolated from the discrete positions for intermediate positions between the discrete positions.

Figure 26:
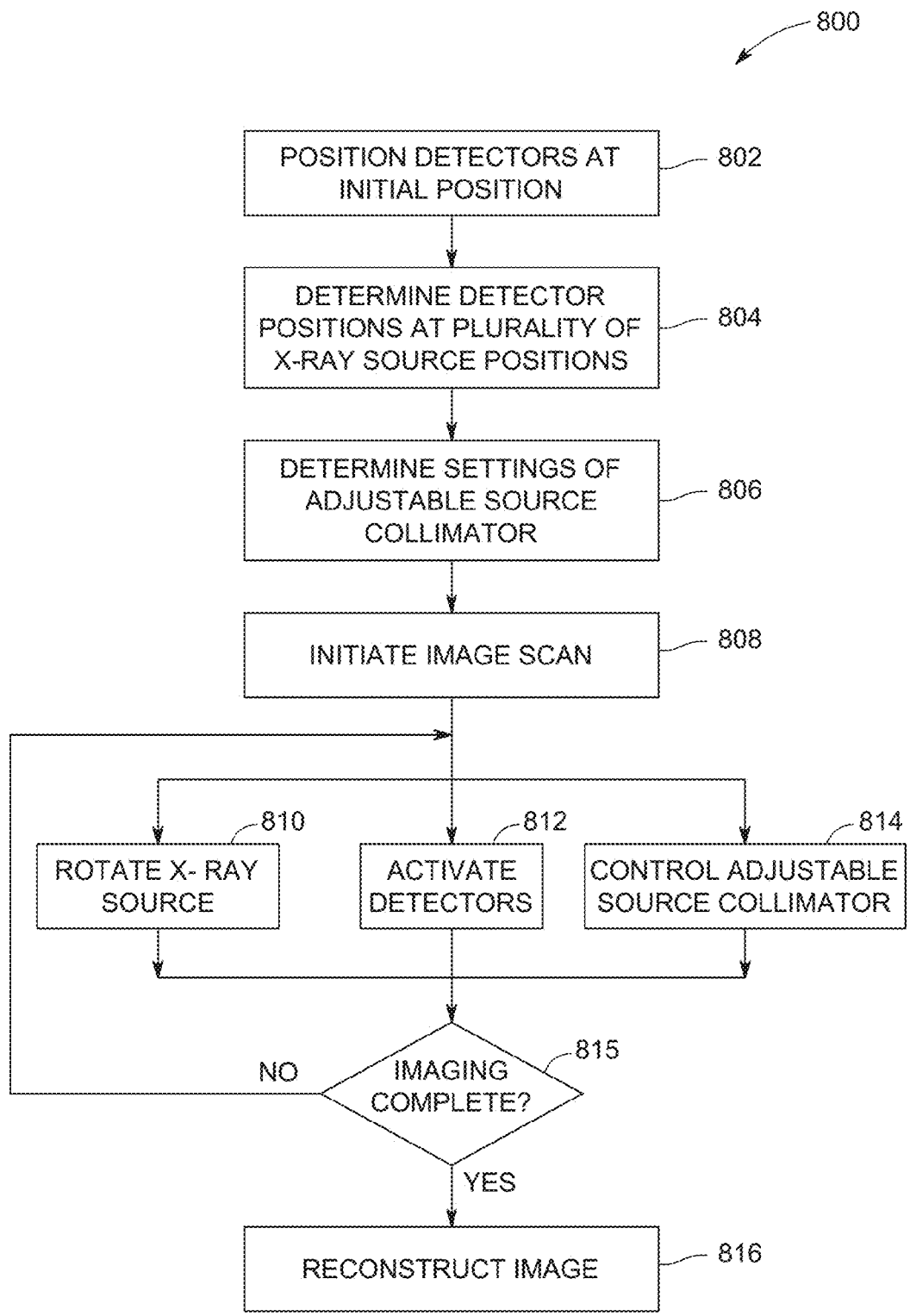
FIG. 26 shows a flowchart of a method, according to an embodiment.

FIG. 26 provides a flowchart of a method 800 for imaging an object, in accordance with various embodiments. The method 800, for example, may employ or be performed by structures or aspects of various embodiments (e.g., systems and/or methods and/or process flows) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 800 may be able to be used as one or more algorithms to direct hardware (e.g., one or more aspects of the processing unit 350) to perform one or more operations described herein.

At 802, detectors (e.g., detectors 320 of system 300) are positioned at an initial position corresponding to a desired position at a beginning point of a scan of an object to be imaged. In some embodiments, the detectors may remain fixed during rotation of an x-ray source and acquisition of CT information, while in other embodiments the detectors may change position during CT information acquisition.

At 804, the positions of the detectors relative to the x-ray source at a plurality of rotational positions of the x-ray source are determined. The position information determined may include the number of detectors within a field of view of the x-ray source at a particular rotational position of the x-ray source, the identity and functionality of the detectors within the field of view, the radial distance of the detectors from the center of the bore, the orientation of the detector surfaces, and the circumferential location of the detectors. As discussed herein, the positions of the detectors may be determined based on a priori knowledge of the detectors and/or using a test or simulated run of the imaging process without the object to be imaged disposed in the bore. Further, the positions of the detectors at certain rotational positions of the x-ray source may be interpolated from positions determined from other rotational positions.

At 806, settings for an adjustable source collimator (e.g., adjustable source collimator 340) are determined as a function of rotational position of the x-ray source. For example, based on the determined positions of the detectors relative to the x-ray source as a function of rotational position of the x-ray source, the portions of a fan angle emitted by the x-ray source that will impact the detectors within the field of view may be determined, and the portions of the fan angle that will not impact the detectors may also be determined, as a function of rotational position of the x-ray source. Settings for the adjustable source collimator may then be determined to provide passage of x-rays through the adjustable source collimator corresponding to the determined portions of the fan angle that will impact detector surfaces. For example, the adjustable source collimator settings may be determined or selected to provide passage of all portions of the fan angle that will impact detector surfaces, along with a safety margin or padding. With the positions of the detectors relative to the x-ray source changing with the rotation of the x-ray source about the object to be imaged relative to the detectors, the adjustable source collimator settings may also be determined based on the rotational position of the x-ray source relative to the detectors.

At 808, an image scan is initiated relative to an object placed within the gantry bore. It may be noted that in some embodiments an emission scan may be performed at or near the same time as the CT scan. For example, detectors within the field of view of the x-ray source may acquire CT only or CT and emission information and detectors outside if the field of view of the x-ray source may acquire nuclear medicine emission data.

At 810, the x-ray source is rotated about the object to be imaged relative to the detectors. The x-ray source may be rotated while the detectors do not rotate about the bore, the detectors may be rotated while the x-ray source does not rotate about the bore, or both the x-ray source and the detectors may be rotated about the bore (e.g., in opposite directions). As discussed herein, rotation of the x-ray source and detectors in opposite directions may be utilized to reduce an amount of time for acquisition of imaging information.

At 812, as the x-ray source rotates about the bore relative to the detectors, detectors are activated for CT acquisition. For example, as the x-ray source rotates relative to the detectors, those detectors that enter the field of view of the x-ray source may be activated (or switched from an emission mode of acquisition to a CT mode of acquisition), and those detectors that leave the field of view of the x-ray source may be de-activated (or switched from a CT mode of acquisition to an emission mode of acquisition). The CT information acquired by the detectors may be used to generate a CT image and/or generate additional image correction information that can be applied to an emission image.

At 814, as the x-ray source rotates about the bore relative to the detectors, the adjustable source collimator is controlled to provide passage of x-rays to detectors within the field of view while reducing dosage by blocking at least a portion of x-rays that will not impact the detectors. The particular settings may be determined based on the positions of the detectors determined at 804. For instance, based on the positions of the detectors determined at 804, angles of gaps (and/or other measures of the position and extent of gaps) between detectors may be determined, and the adjustable source collimator controlled to block at least a portion of the radiation that would otherwise pass through the gaps between detectors. Additionally or alternatively, in some embodiments, areas of the fan beam from the x-ray source that are outside of the patient may also be detected or determined, with the adjustable source collimator controlled to block all or a portion of the fan beam that may pass outside of the patient. It may be noted the determination of control actions may further take into account the specific type or characteristics of the adjustable source collimator (e.g., configuration or type of openings and blocking portions, numbers and relative sizes of openings and blocking portions, range of sizes of openings and blocking portions, available speed of adjustment for openings, available precision of adjustment for openings, or the like). In various embodiments, the settings determined at 806 may be implemented during rotation of the x-ray source. The settings may be specified as a function of position of the x-ray source, with the position of the x-ray source determined using a sensor associated with the x-ray source during rotation of the x-ray source, and with the settings varied or controlled using the position of the x-ray source as an input. Thus, x-rays that would otherwise pass through the imaged object, and add patient dose, are now blocked by the source collimator.

At 815, it is determined if imaging is complete. If imaging is not complete, the method 800 may return to steps 810, 812, 814 for additional acquisition of imaging information. If imaging is complete, the method 800 proceeds to 816. At 816, after a desired amount of rotation of the x-ray source and acquisition of CT information, an image can be reconstructed using the CT and/or emission information acquired during the scan. The CT data can also be used to correct the image from the emission data scan as shown in FIGS. 8 and 9 above.

As used herein, the term "computer," "processor," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An imaging system comprising:
    a gantry having a bore extending therethrough;
    a plurality of image detectors attached to the gantry and radially spaced apart along a circumference of the bore at one or more predetermined intervals such that gaps exist between adjacent image detectors along the circumference of the bore, wherein at least one image detector detects both emission radiation and x-ray radiation;
    an x-ray source attached to the gantry, wherein the x-ray source rotates about the bore of the gantry and transmits x-rays across the bore towards at least two of the image detectors;

an adjustable source collimator interposed between the x-ray source and a center of the bore, the adjustable source collimator configured to block a portion of the x-rays produced by the x-ray source along a fan angle in a scanning direction defined by the circumference of the bore, wherein the fan angle extends along a direction of rotation of the x-ray source; and at least one processor operably coupled to the adjustable source collimator, the at least one processor configured to control the adjustable source collimator to dynamically adjust a range of x-rays that are blocked by the adjustable source collimator along the fan angle during rotation of the x-ray source and transmission of x-rays from the x-ray source and acquisition of computed tomography (CT) information by the at least two of the image detectors.

2. The imaging system of claim 1, wherein the at least one processor is configured to dynamically adjust outer boundaries of the fan angle to correspond to a range defined by the at least two of the image detectors.

3. The imaging system of claim 1, wherein the adjustable source collimator comprises a plurality of openings separated by blocking portions along the fan angle.

4. The imaging system of claim 3, wherein the openings have a fixed width.

5. The imaging system of claim 4, wherein the adjustable source collimator comprises a movable plate having the openings formed therethrough, the movable plate configured to be translated laterally with respect to the x-ray source.

6. The imaging system of claim 3, wherein at least one of the openings has an adjustable width.

7. The imaging system of claim 6, wherein the adjustable source collimator comprises a rotary member, the adjustable width varying during rotation of the rotary member.

8. The imaging system of claim 1, wherein the x-ray source and the at least two detectors are configured to rotate in opposite directions about the bore during the acquisition of the CT information.

9. The imaging system of claim 1, wherein the at least one processor is configured to identify at least one of the detectors as an inoperable detector, and to control the adjustable source collimator to block radiation directed toward the inoperable detector.

10. The imaging system of claim 1, wherein the at least one processor is configured to identify at least one detector location for which a detector is not installed, and to control the adjustable source collimator to block radiation directed toward the at least one detector location for which a detector is not installed.

11. A method of acquiring computed tomography (CT) information with an imaging system having a gantry having a bore extending therethrough, a plurality of image detectors attached to the gantry and radially spaced apart along a circumference of the bore at one or more predetermined intervals such that gaps exist between adjacent image detectors along the circumference of the bore, an x-ray source attached to the gantry and configured to rotate about the bore of the gantry, wherein the x-ray source transmits x-rays across the bore towards at least two of the image detectors, and an adjustable source collimator interposed between the x-ray source and a center of the bore, the adjustable source collimator configured to block a portion of the x-rays produced by the x-ray source along a fan angle in a scanning direction defined by the circumference of the bore, wherein the fan angle extends along a direction of rotation of the x-ray source the method comprising:

determining positions of the image detectors relative to the x-ray source at a plurality of rotational positions of the x-ray source about the bore; and controlling the adjustable source collimator, based on the determined positions of the image detectors, to dynamically adjust a range of x-rays that are blocked by the adjustable source collimator along the fan angle during rotation of the x-ray source and transmission of x-rays from the x-ray source as the x-ray source is rotated about the gantry relative to the image detectors and acquisition of the CT information by the at least two of the image detectors.

12. The method of claim 11, further comprising:

determining, using the determined positions of the image detectors, detected and non-detected portions of the fan angle for the plurality of rotational positions, wherein the detected portions impinge upon the image detectors and the non-detected portions do not impinge upon the image detectors; and controlling the adjustable source collimator to adjust the range of x-rays using the determined detected and non-detected portions of the fan angle.

13. The method of claim 11, wherein determining the positions of the image detectors comprises determining the positions based on reception of x-rays during a test rotation of the x-ray source.

14. The method of claim 11, wherein controlling the adjustable source collimator comprises adjusting outer boundaries of the fan angle to correspond to a range defined by the at least two of the image detectors.

15. The method of claim 11, wherein the adjustable source collimator comprises a movable plate having a plurality of fixed width openings formed therethrough separated by blocking portions along the fan angle, wherein controlling the adjustable source collimator comprises moving the movable plate relative to the x-ray source during the transmission of x-rays from the x-ray source as the x-ray source is rotated about the gantry relative to the image detectors.

16. The method of claim 11, wherein the adjustable source collimator comprises plural adjustable openings separated by blocking portions along the fan angle, wherein controlling the adjustable source collimator comprises varying a width of at least one of the adjustable openings during transmission of x-rays from the x-ray source as the x-ray source is rotated about the gantry relative to the image detectors.

17. The method of claim 16, wherein the adjustable source collimator comprises a rotary member, wherein controlling the adjustable source collimator comprises rotating the rotary member to vary the width of the at least one of the adjustable openings.

18. A system comprising:

an adjustable source collimator configured to be interposed between an x-ray source and a center of a bore of a gantry of an imaging system, wherein the x-ray source is configured to rotate about the center of the gantry, the adjustable source collimator configured to block a portion of the x-rays produced by the x-ray source along a fan angle in a scanning direction defined by a circumference of the bore, wherein the fan angle extends along a direction of rotation of the x-ray source;

wherein the adjustable source collimator comprises a plurality of openings separated by blocking portions along the fan angle;

a plurality of image detectors configured to detect x-ray radiation, the plurality of image detectors attached to the gantry and radially spaced apart along the circumference of the bore at one or more predetermined intervals such that gaps exist between adjacent image detectors along the circumference of the bore, wherein at least one image detector detects both emission radiation and x-ray radiation; and at least one processor operably coupled to the adjustable source collimator, the at least one processor configured to control the adjustable source collimator to dynamically adjust a range of x-rays that are blocked by the adjustable source collimator along the fan angle during rotation of the x-ray source and transmission of x-rays from the x-ray source and acquisition of computed tomography (CT) information by the at least two of the image detectors.

19. The system of claim 18, wherein at least one of the openings has an adjustable width.

20. The system of claim 19, wherein the adjustable source collimator comprises a rotary member, the adjustable width varying during rotation of the rotary member.

21. The system of claim 18, wherein the adjustable source collimator comprises a movable plate having a plurality of fixed width openings formed therethrough separated by the blocking portions along the fan angle, wherein the at least one processor is configured to control the adjustable source collimator to adjust the range of x-rays by moving the movable plate relative to the x-ray source during the transmission of x-rays from the x-ray source as the x-ray source is rotated about the gantry relative to the image detectors.

22. The system of claim 18, wherein at least one of the openings has an adjustable width, wherein the adjustable source collimator comprises a rotary member, the adjustable width varying during rotation of the rotary member, wherein the at least one processor is configured to control the adjustable source collimator by rotating the rotary member during the transmission of x-rays from the x-ray source as the x-ray source is rotated about the gantry relative to the image detectors.

23. A method of acquiring computed tomography (CT) information with an imaging system having a gantry having a bore extending therethrough, a plurality of image detectors attached to the gantry and radially spaced apart along a circumference of the bore at one or more predetermined intervals such that gaps exist between adjacent image detectors along the circumference of the bore, an x-ray source attached to the gantry, wherein the x-ray source transmits x-rays across the bore, and an adjustable source collimator interposed between the x-ray source and a center of the bore, wherein the x-ray source rotates about the bore, the adjustable source collimator configured to block a portion of the x-rays produced by the x-ray source along a fan angle in a scanning direction defined by the circumference of the bore, wherein the fan angle extends along a direction of rotation of the x-ray source the method comprising:

determining positions of the image detectors relative to the x-ray source at a plurality of rotational positions of the x-ray source about the bore;

rotating the x-ray source relative to the image detectors about an object to be imaged disposed within the bore;

activating the image detectors based on detector position as the x-ray source rotates about the object to be imaged to provide at least two active detectors for each rotational position; and controlling the adjustable source collimator, based on the determined positions of the image detectors, to dynamically adjust a range of x-rays to permit passage of x-rays to the at least two active detectors for each rotational position and to inhibit passage of x-rays that are not directed toward the at least two active detectors for each rotational position during transmission of x-rays from the x-ray source as the x-ray source is rotated about the gantry relative to the image detectors and acquisition of the CT information.

24. The method of claim 23, wherein the at least two active detectors are activated based on entry into a field of view of the x-ray source.

25. The method of claim 23, wherein activating the at least two active detectors comprises switching the at least two active detectors to a CT mode of acquisition.

26. The method of claim 23, further comprising de-activating the at least two active detectors based on exiting from a field of view of the x-ray source.

27. The method of claim 26, wherein de-activating the at least two active detectors comprises switching the at least two active detectors from a CT mode of acquisition.

* * * * *